(12) United States Patent
Morgan

(10) Patent No.: US 8,105,398 B2
(45) Date of Patent: Jan. 31, 2012

(54) PRODUCTION OF ESTER-BASED FUELS SUCH AS BIODIESEL FROM RENEWABLE STARTING MATERIALS

(75) Inventor: William Douglas Morgan, Richmond, CA (US)

(73) Assignee: Endicott Biofuels II, LLC, Houston, TX (US)

( * ) Notice: Subject to any disclaimer, the term of this patent is extended or adjusted under 35 U.S.C. 154(b) by 655 days.

(21) Appl. No.: 12/172,649

(22) Filed: Jul. 14, 2008

(65) Prior Publication Data

US 2009/0056201 A1    Mar. 5, 2009

Related U.S. Application Data

(60) Provisional application No. 60/968,222, filed on Aug. 27, 2007.

(51) Int. Cl.
*C10L 1/18*    (2006.01)
(52) U.S. Cl. .............................. 44/308; 44/300; 44/307
(58) Field of Classification Search .................... 44/306, 44/308, 605, 300, 307; 424/484; 210/644; 554/164
See application file for complete search history.

(56) References Cited

U.S. PATENT DOCUMENTS

| | | | |
|---|---|---|---|
| 2,320,844 A | 6/1943 | Black | |
| 2,486,630 A | 11/1949 | Brown | 554/160 |
| 3,707,361 A | 12/1972 | Annable | |
| 4,193,770 A | 3/1980 | Chase et al. | |
| 4,698,186 A | 10/1987 | Jeromin et al. | |
| 5,308,365 A | 5/1994 | Kesling et al. | |
| 5,399,731 A | 3/1995 | Wimmer | 554/167 |
| 5,536,856 A * | 7/1996 | Harrison et al. | 554/164 |
| 5,578,090 A | 11/1996 | Bradin | |
| 6,045,762 A | 4/2000 | Chuang et al. | |
| 6,174,501 B1 | 1/2001 | Noureddini | 422/189 |
| 6,299,655 B1 | 10/2001 | Steckel et al. | 44/331 |
| 6,399,801 B1 | 6/2002 | Smith et al. | 554/156 |
| 6,630,430 B1 | 10/2003 | Anantaneni et al. | |
| 6,855,838 B2 | 2/2005 | Haas et al. | |
| 6,965,044 B1 | 11/2005 | Hammond et al. | 554/169 |
| 7,045,100 B2 | 5/2006 | Ergun et al. | 422/129 |
| 7,091,367 B2 | 8/2006 | Moritz et al. | |
| 7,635,398 B2 * | 12/2009 | Bertram et al. | 44/605 |
| 7,705,170 B2 | 4/2010 | Geier et al. | |
| 2002/0184814 A1 | 12/2002 | Manka | |

(Continued)

FOREIGN PATENT DOCUMENTS

JP    06-313188    11/1994

(Continued)

OTHER PUBLICATIONS

Takahiro, K. et al., Production of Fatty acid Ester, JP 06-313188, English translation (8 pages), Nov. 8, 1994.

(Continued)

*Primary Examiner* — Michael Marcheschi
*Assistant Examiner* — Chantel Graham
(74) *Attorney, Agent, or Firm* — King & Spalding LLP; Kyle M. Zeller

(57) ABSTRACT

Production of ester-based fuels such as biodiesel or jet fuel from renewable starting materials such as lignocellulosic material or algae is disclosed. Pulping and saccharification of the renewable starting materials produces carboxylic acids such as fatty acids or rosin acids, which are esterified via a gas sparged, slurry form of heterogeneous reactive distillation to yield ester-based fuels.

13 Claims, 13 Drawing Sheets

U.S. PATENT DOCUMENTS

| | | | |
|---|---|---|---|
| 2004/0060226 A1 | 4/2004 | Bongart et al. | |
| 2004/0106813 A1 | 6/2004 | Moritz et al. | |
| 2004/0254387 A1 | 12/2004 | Luxem et al. | |
| 2005/0039384 A1 | 2/2005 | Gormley | 44/397 |
| 2005/0081436 A1 | 4/2005 | Bertram et al. | |
| 2005/0261144 A1 | 11/2005 | Notari et al. | 508/462 |
| 2006/0016751 A1* | 1/2006 | Ali et al. | 210/644 |
| 2006/0048443 A1 | 3/2006 | Filippini et al. | 44/301 |
| 2006/0246563 A1 | 11/2006 | Eroma et al. | 435/158 |
| 2006/0264681 A1 | 11/2006 | Obenaus et al. | 568/671 |
| 2006/0293533 A1 | 12/2006 | Iyer | 554/174 |
| 2007/0033865 A1 | 2/2007 | Caprotti et al. | 44/640 |
| 2007/0049727 A1 | 3/2007 | Pollock et al. | 530/205 |
| 2007/0124992 A1 | 6/2007 | Reaney et al. | 44/389 |
| 2007/0129565 A1 | 6/2007 | Sutton et al. | 560/190 |
| 2007/0130820 A1* | 6/2007 | Chatterjee et al. | 44/306 |
| 2007/0137097 A1 | 6/2007 | Ikura | 44/308 |
| 2007/0142652 A1 | 6/2007 | Arumughan et al. | 552/540 |
| 2007/0158270 A1 | 7/2007 | Geier et al. | 210/656 |
| 2007/0238905 A1 | 10/2007 | Arredondo et al. | |
| 2007/0260077 A1 | 11/2007 | Elliott | 554/174 |
| 2007/0277429 A1* | 12/2007 | Jackam et al. | 44/308 |
| 2007/0277432 A1 | 12/2007 | Jackam et al. | |
| 2008/0051592 A1 | 2/2008 | McNeff et al. | 554/170 |
| 2008/0051599 A1 | 2/2008 | Adami et al. | 560/129 |
| 2008/0071125 A1 | 3/2008 | Li | |
| 2009/0188157 A1 | 7/2009 | Holloway et al. | |
| 2010/0047884 A1 | 2/2010 | De Greyt et al. | |
| 2010/0136113 A1* | 6/2010 | Steer et al. | 424/484 |

FOREIGN PATENT DOCUMENTS

| | | | |
|---|---|---|---|
| WO | WO 90/08127 | | 7/1990 |
| WO | WO 95/25152 | | 9/1995 |
| WO | WO2004080942 | * | 9/2004 |
| WO | WO 2006/093896 | | 9/2006 |
| WO | WO 2007/050030 | | 5/2007 |

OTHER PUBLICATIONS

Title 26 Section 6426 Credit for alcohol fuel, biodiesel, and alternative fuel mixtures.
26 U.S.C § 40A. Jan. 3, 2006. Downloaded on Sep. 30, 2008 from <http://uscode.house.gov/uscode-cgi/fastweb.exe?getdoc+uscview+usclass+2465+0++%28%29%20%20>.
Chongkhong, S et al., "Biodiesel production by esterification of palm fatty acid distillate," Biomass and Bioenergy, vol. 31, issue 8, pp. 563-568, Aug. 2007, available online May 7, 2007.
Dasari, M.A., "Catalytic Conversion of Glycerol and Sugar Alcohols to Value-Added Products." PhD Thesis. University of Missouri-Columbia. May 2006. Downloaded from <<edt.missouri.edu/winter2006/dissertation/dasariM-051506-D4163/research.pdf.
Enviromental Protection Agency, "Regulation of Fuels and Fuel Additives: Renewable Fuel Standard Program; Final Rule", 10 CFR Part 80 Federal Register, vol. 72, No. 83, pp. 23944-23946, 23960, May 1, 2007.
Lotero et al., "The Catalysis of Biodiesel Synthesis," Catalysis, vol. 19, p. 75, 2006.
Ma et al., "Biodiesel Production: a review" Bioresource Technology, vol. 70, pp. 1-15, Oct. 1999.
U.S. Appl. No. 12/172,649, filed Jul. 14, 2008, William Morgan.
U.S. Appl. No. 12/048,028, filed Mar. 13, 2008, William Morgan.
U.S. Appl. No. 12/182,991, filed Jul. 30, 2008, William Morgan.
U.S. Appl. No. 12/172,717, filed Jul. 14, 2008, William Morgan.
U.S. Appl. No. 12/172,820, filed Jul. 14, 2008, William Morgan.
U.S. Appl. No. 12/172,875, filed Jul. 14, 2008, William Morgan.
U.S. Appl. No. 12/174,314, filed Jul. 16, 2008, William Morgan.
U.S. Appl. No. 12/174,392, filed Jul. 16, 2008, William Morgan.
U.S. Appl. No. 12/047,585, filed Mar. 13, 2008, William Morgan.
Takahiro, K. et al., Method for Production Fatty Acid Ester, H6-313188, English translation (4 pages).

* cited by examiner

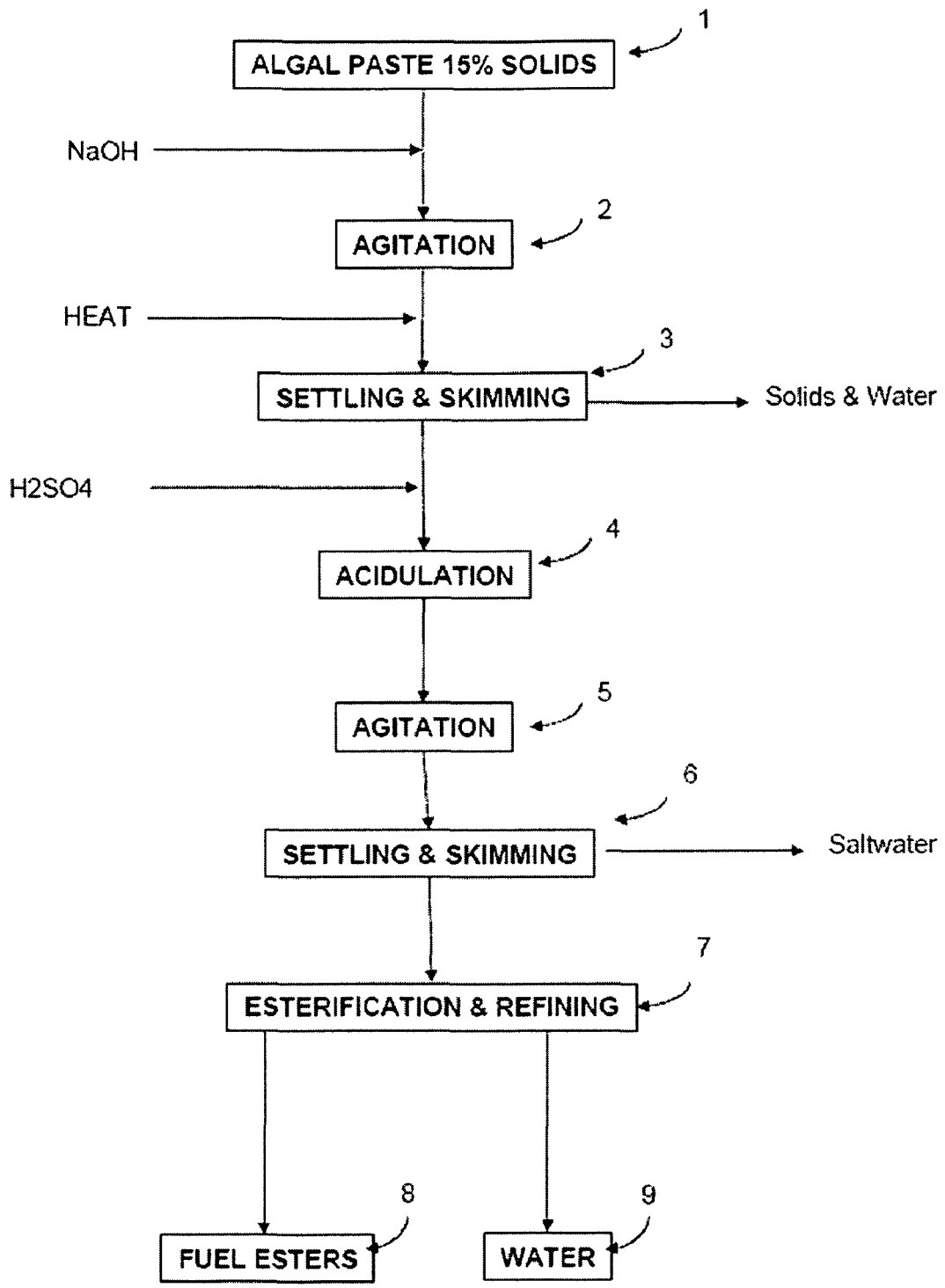

FIGURE 7a

Table 1

| FEEDSTUFF | EE % | FEEDSTUFF | EE % |
|---|---|---|---|
| Alfalfa Cubes | 2 | Canarygrass Hay | 2.7 |
| Alfalfa Dehydrated 17% CP | 3 | Canola Meal Solvent | 4 |
| Alfalfa Fresh | 3 | Carrot Pulp | 7.8 |
| Alfalfa Hay Early Bloom | 2.5 | Carrot Root Fresh | 1.4 |
| Alfalfa Hay Full Bloom | 2 | Carrot Tops | 3.8 |
| Alfalfa Hay Mature | 1.3 | Cattle Manure Dried | 2.6 |
| Alfalfa Hay Midbloom | 2.3 | Cheatgrass Fresh Immature | 2.7 |
| Alfalfa Leaf Meal | 2.7 | Citrus Pulp Dried | 2.2 |
| Alfalfa Seed Screenings | 10.5 | Clover Ladino Fresh | 4.8 |
| Alfalfa Silage | 3 | Clover Ladino Hay | 2 |
| Alfalfa Silage Wilted | 3 | Clover Red Fresh | 4 |
| Alfalfa Stems | 1.3 | Clover Red Hay | 2.5 |
| Almond Hulls | 3.3 | Clover Sweet Hay | 2.4 |
| Apple Pomace Dried | 5.2 | Coconut Meal | 6.7 |
| Apple Pomace Wet | 5.6 | Coffee Grounds | 15 |
| Artichoke Tops (Jerusalem) | 1.1 | Corn and Cob Meal | 3.7 |
| Avocado Seed Meal | 1.2 | Corn Bran | 6.3 |
| Bahiagrass Hay | 1.9 | Corn Cannery Waste | 3 |
| Bakery Product Dried | 11 | Corn Cobs | 0.5 |
| Barley Feed Pearl Byproduct | 3.9 | Corn Fodder | 2.4 |
| Barley Grain | 2.1 | Corn Gluten Feed | 3.2 |
| Barley Grain 2-row | 2.3 | Corn Gluten Meal, 41% CP | 3.2 |
| Barley Grain 6-row | 2.2 | Corn Gluten Meal, 60% CP | 2.6 |
| Barley Grain Lt.Wt. (42-44 lbs./bu.) | 2.3 | Corn Grain, High Moisture | 4 |
| Barley Grain Screenings | 2.6 | Corn Grain, High Oil | 6.9 |
| Barley Grain, Steam Flaked | 2.1 | Corn Grain, Hi-Lysine | 4.4 |
| Barley Grain, Steam Rolled | 2.1 | Corn Grain, Rolled | 4.3 |
| Barley Hay | 2.1 | Corn Grain, Steam Flaked | 4.1 |
| Barley Silage | 3 | Corn Grain, Whole | 4.3 |
| Barley Silage Mature | 3.5 | Corn Screenings | 4.3 |
| Barley Straw | 1.9 | Corn Silage Mature Well Eared | 3.1 |
| Beans Navy Cull | 1.4 | Corn Silage Milk Stage | 2.8 |
| Beet Pulp Dried | 0.7 | Corn Silage Sweet Corn | 5 |
| Beet Pulp Dried with Molasses | 0.6 | Corn Stover Mature (Stalks) | 1.3 |
| Beet Pulp Wet | 0.7 | Corn Whole Plant Pelleted | 2.4 |
| Beet Pulp Wet with Molasses | 0.6 | Cotton Gin Trash (Burrs) | 2 |
| Beet Top Silage | 2 | Cottonseed Hulls | 1.9 |
| Beet Tops (Sugar) | 1.5 | Cottonseed Meal, Mech. 41% CP | 5 |
| Bermudagrass Coastal Dehydrated | 3.8 | Cottonseed Meal, Solvent 41% CP | 1.8 |
| Bermudagrass Coastal Hay | 2.1 | Cottonseed, Whole | 17.8 |
| Bermudagrass Hay | 1.9 | Cottonseed, Whole, Delinted | 22.2 |
| Bermudagrass Silage | 1.9 | Cottonseed, Whole, Extruded | 9.5 |
| Birdsfoot Trefoil Fresh | 4.4 | Crab Waste Meal | 3 |
| Birdsfoot Trefoil Hay | 2.2 | Crambe Meal, Mech. | 17 |
| Blood Meal, Swine/Poultry | 1.4 | Crambe Meal, Solvent | 1.4 |
| Bluegrass KY Fresh Early Bloom | 3.9 | Cranberry Pulp Meal | 15.7 |
| Bluegrass Straw | 1.1 | Crawfish Waste Meal | |
| Bluestem Fresh Mature | 2.5 | Distillers Corn Stillage | 8.1 |
| Bone Meal Steamed, Swine/Poultry | 11.6 | Distillers Dried Solubles | 9.2 |
| Bread By-product | 3.2 | Distillers Grain, Barley | 3.7 |
| Brewers Grains Dried | 8.2 | Distillers Grain, Corn with Solubles | 10.6 |
| Brewers Grains Wet | 7.6 | Distillers Grain, Corn, Dry | 10.5 |
| Brewers Yeast Dried | 1 | Distillers Grain, Corn, Wet | 10.5 |
| | | Distillers Grain, Sorghum with Solubles | 10 |
| Bromegrass Fresh Immature | 4.1 | Distillers Grain, Sorghum, Dry | 10 |
| Bromegrass Hay | 2.3 | Distillers Grain, Sorghum, Wet | 10 |
| Bromegrass Haylage | 2.5 | Distillers Grains, Wet | 9.6 |
| Buckwheat Grain | 2.8 | | |
| Buttermilk Dried | 5 | Elephant (Napier) grass hay, chopped | 2 |
| Cactus | 2.1 | Fat, Animal, Poultry, Vegetable | 99 |
| | | Feather Meal Hydrolyzed | 6.5 |

FIGURE 7b

| FEEDSTUFF | EE % | FEEDSTUFF | EE % |
|---|---|---|---|
| Fescue (Red) Straw | 1.1 | Rice Bran | 17 |
| Fescue KY 31 Fresh | 5.5 | Rice Grain | 1.9 |
| Fescue KY 31 Hay Early Bloom | 6.6 | Rice Hulls | 0.9 |
| Fescue KY 31 Hay Mature | 5 | Rice Mill By-product | 5.7 |
| Fish Meal | 8 | Rice Polishings | 14 |
| Garbage Municipal Cooked | 20 | Rice Straw | 1.4 |
| Grain Dust | 2.2 | Rice Straw Ammoniated | 1.3 |
| Grain Screenings | 5.5 | Rye Grain | 1.7 |
| Grape Pomace Stemless | 7.5 | Rye Grass Hay | 3.3 |
| Grass Hay | 3 | Rye Grass Silage | 3.3 |
| Grass Silage | 3.4 | Rye Straw | 1.5 |
| Guar Meal | 3.9 | Safflower Meal Dehulled Solvent | 0.6 |
| Hominy Feed | 6.1 | Safflower Meal Solvent | 1.2 |
| Hop Leaves | 3.6 | Sagebrush Fresh | 9.2 |
| Hop Vine Silage | 3.1 | Sanfoin Hay | 3.1 |
| Hops Spent | 4.5 | Shrimp Waste Meal | 5.5 |
| Kelp Dried | 0.5 | Sorghum Grain (Milo) Ground | 3.1 |
| Kenaf Hay | 2.9 | Sorghum Silage | 2.7 |
| Kochia Fresh | 1.2 | Sorghum Stover | 1.9 |
| Kochia Hay | 1.7 | Sorhum Grain (Milo) Flaked | 3.1 |
| Kudzu Hay | 2.6 | Soybean Hay | 2.2 |
| Lespedeza Fresh Early Bloom | 2 | Soybean Hulls | 2.6 |
| Lespedeza Hay | 3 | Soybean Meal Solvent 44% CP | 1.6 |
| Linseed Meal Solvent | 1.9 | Soybean Meal Solvent 49% CP | 1.2 |
| Meadow Hay | 2.5 | Soybean Mill Feed | 2 |
| Meat and Bone Meal, Swine/Poultry | 10 | Soybean Straw | 1.4 |
| Meat Meal, Swine/Poultry | 10.5 | Soybeans Whole | 18.8 |
| Milk, Dry, Skim | 1 | Soybeans Whole, Extruded | 18.8 |
| Mint Slug Silage | 1.8 | Soybeans Whole, Roasted | 18.8 |
| Molasses Beet | 0.2 | Spelt Grain | 2.1 |
| Molasses Cane | 0.8 | Sudangrass Fresh Immature | 3.9 |
| Molasses Cane Dried | 0.3 | Sudangrass Hay | 1.8 |
| Molasses Citrus | 0.3 | Sudangrass Silage | 3.1 |
| Molasses Wood, Hemicellulose | 0.7 | Sugar Cane Bagasse | 0.7 |
| Molasses, Cond. Fermentation Solubles | | Sunflower Seed Hulls | 2.2 |
| Oat Grain | 5 | Sunflower Seed Meal Solvent | 2.5 |
| Oat Grain, Steam Flaked | 4.9 | Sunflower Seed Meal with Hulls | 2.4 |
| Oat Groats | 6.6 | Tapioca Meal | 0.8 |
| Oat Hay | 2.3 | Timothy Fresh, Pre-bloom | 3.8 |
| Oat Hulls | 1.5 | Timothy Hay, Early Bloom | 2.7 |
| Oat Middlings | 6 | Timothy Hay, Full Bloom | 2.6 |
| Oat Mill By-product | 2.6 | Timothy Silage | 3.4 |
| Oat Silage | 3.2 | Tomato Pomace Dried | 10.6 |
| Oat Straw | 2.3 | Triticale Grain | 2.4 |
| Orange Pulp Dried | 1.8 | Triticale Hay | |
| Orchardgrass Fresh Early Bloom | 4 | Triticale Silage | 3.6 |
| Orchardgrass Hay | 3.3 | Turnip Roots | 1.5 |
| Pea Straw | 1.3 | Turnip Tops (Purple) | 2.6 |
| Pea Vine Hay | 1.8 | Vetch Hay | 1.8 |
| Pea Vine Silage | 3.3 | Wheat Bran | 4.5 |
| Peanut Hulls | 1.5 | Wheat Fresh, Pasture | 4 |
| Peanut Meal Solvent | 3.6 | Wheat Grain | 2.3 |
| Peanut Skins | 22 | Wheat Grain, Hard | 2 |
| Pearl Millet Grain | 4.5 | Wheat Grain, Soft | 2 |
| Peas Cull | 1.5 | Wheat Grain, Sprouted | 2 |
| Pineapple Bran | 1.5 | Wheat Grain, Steam Flaked | 2.3 |
| Pineapple Greenchop | 2.6 | Wheat Hay | 2 |
| Pineapple Presscake | 0.9 | Wheat Middlings | 4.6 |
| Potato Vine Silage | 3.7 | Wheat Mill Run | 4.4 |
| Potato Waste Dried | 0.5 | Wheat Shorts | 5.4 |
| Potato Waste Filter Cake | 7.7 | Wheat Silage | 3.2 |
| Potato Waste Wet | 1.5 | Wheat Straw | 1.8 |
| Potato Waste Wet with Lime | 0.3 | Wheat Straw, Ammoniated | 1.5 |
| Potatoes Cull | 0.4 | Wheatgrass Crested Fresh Early Bloom | 1.6 |
| Poultry By-product Meal | 14.5 | Wheatgrass Crested Fresh Full Bloom | 1.6 |
| Poultry Manure Dried | 2.1 | Wheatgrass Crested Hay | 2.4 |
| Prairie Hay | 2 | Whey Dried | 1 |
| Pumpkins, Cull | 8.9 | | |

FIGURE 8

Table 2

| Process | Main Mechanism | Major Inputs | Dependence on algae | Relative Cost | Concent. Solids | Energy Inputs |
|---|---|---|---|---|---|---|
| Centrifugation | Accelerated discrete settling | Power Equipment | minor | 10 | > 10% | high |
| Chem. Flocculation | | | | | | |
| Inorganic lime | floc enmeshment | Lime + Mix. | minor | 6 - 8 | 8 - 10% | high |
| alumn | " + destabilize | Alumn + Mix. | minor | 6 - 8 | 8 - 10% | high |
| Polyelectrolytes | " + " + bridging | PE + Mixing | minor | 4 - 6 | 8 - 10% | medium |
| Cross Flow Filtration | Membrane self cleaning | Power Equipment | minor | 4 - 6 | 2 - 6% | high |
| Microstraining | fabric straining "Schmutzdecke" | Power Equipment | high | 0.5 - 1.5 | 2 - 4% | medium |
| High Grad. Mag. Sep. | Adsorption of Magnetic Particle | Power Equipment | Unk. | Unk. | Unk. | Unk. |
| Discrete Sedimentation | Gravity Discrete Settling | Pumping, Clarifier | high | 0.5 - 1 | 1 - 3% | low |
| Bioflocculation | Spontaneous Flocculation | Pumping, Clarifier | high | 0.5 - 1 | 1 - 3% | low |
| Autoflocculation | Ca/Mg ppt. induced floc | Pumping, Clarifier | minor | 0.5 - 1 | 1 - 3% | low |
| Autoconcentration | Phototaxis | Pumping, Clarifier | high | Unk. | Unk. | low? |

FIGURE 9

TABLE 3

CURRENT AVAILABILITY OF BIOMASS FROM AGRICULTURAL LANDS

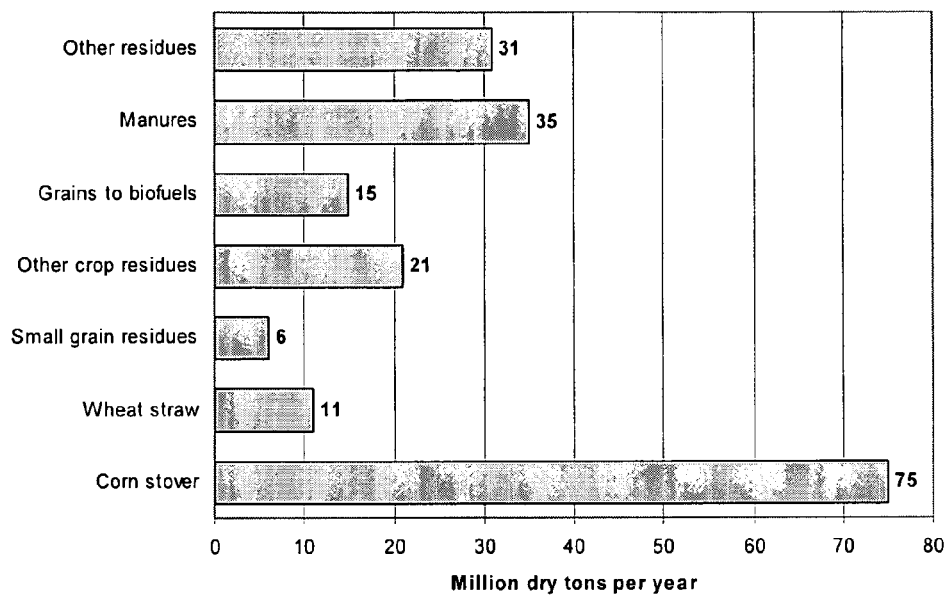

- The total current availability of biomass from cropland is approximately 194 million dry tons/year
- Slightly more than one-fifth of this biomass is currently used.
- Corn stover is a major untapped source of agriculture-derived biomass
- Small grain residues include sorghum, barley, oats, and rice. Other crop residues include cotton, other oil seeds (e.g., sunflower, peanuts, canola), tobacco sugar crops, potatoes, beans, miscellaneous root crops, and double crops. Other residues include secondary agricultural processing residues, MSW, and fats and greases.

FIGURE 10

TABLE 4

AVAILABILITY OF BIOMASS UNDER INCREASED CROP YIELDS AND TECHNOLOGY CHANGES

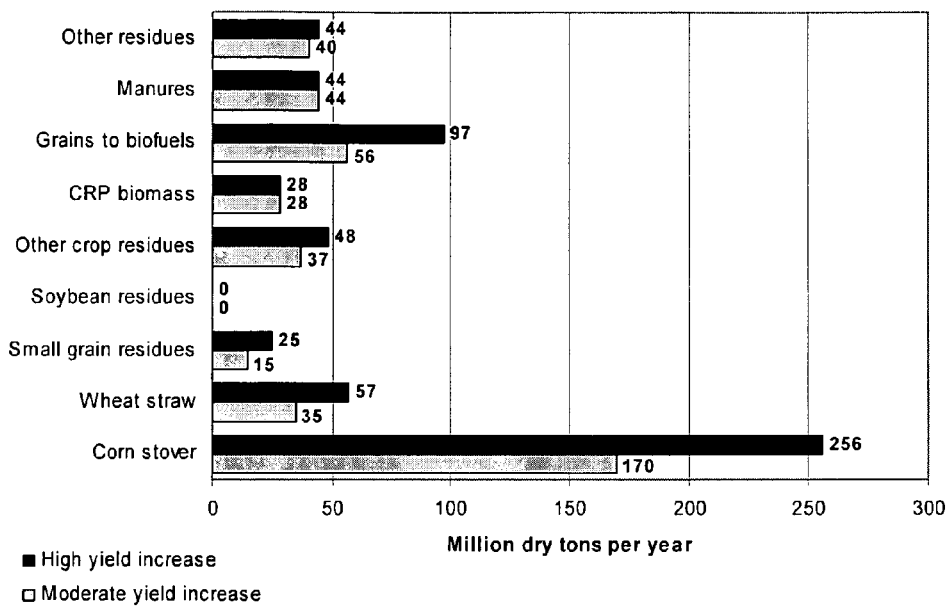

■ High yield increase
□ Moderate yield increase

- Total availability of biomass from cropland ranges from 423 to 5976 million dry tons per year at crop yield increases of 25% (moderate) and 50% (high) for corn and various rates of increase for other crops. Moderate and high changes in tillage practices and residue collection technology and equipment are also assumed. (Quantities shown do not add to 423 and 597 million dry tons due to rounding.)
- No changes in the current allocation of cropland are required to attain these levels of biomass.
- Small grain residues include sorghum, barley, oats, and rice. Other crop residues include cotton, other oil seeds (e.g., sunflower, peanuts, canola), tobacco, sugar crops, potatoes, beans, miscellaneous root crops, and double crops. Other residues include secondary agricultural processing residues, MSW, and fats and grasses.

FIGURE 11

TABLE 5

AVAILABILITY OF BIOMASS UNDER INCREASED CROP YIELDS AND TECHNOLOGY CHANGES
AND INCLUSION OF PERENNIAL CROPS

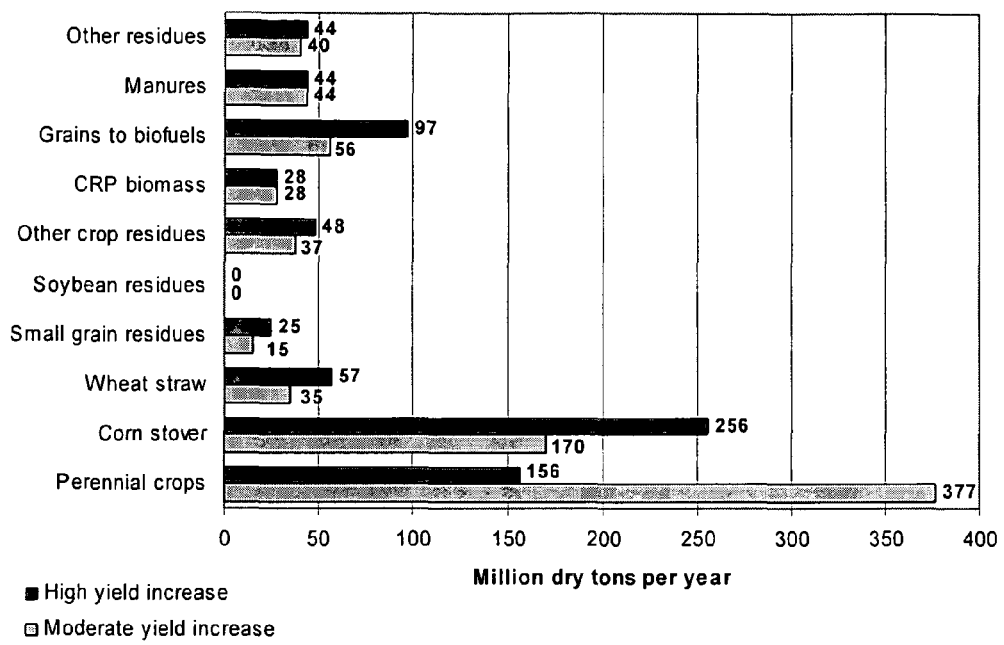

- High yield increase
- Moderate yield increase

- Total availability of biomass from cropland, idle cropland and cropland pasture ranges from 581 to 998 million dry tons per year at crop yield increases of 25% (moderate) and 50% (high) for corn and various rates for other crops. Changes in tillage practice, residue to grain and seed ratios, and residue collection technology and equipment are also assumed. (Quantities shown do not add to 581 million dry tons due to rounding.)

- The allocation of some active cropland, idle cropland, and cropland pasture to perennial crops is required to attain this level of annual biomass production.

- Small grain residues include sorghum, barley, oats, and rice. Other crop residues include cotton, other oil seeds (e.g., sunflower, peanuts, canola), tobacco, sugar crops, potatoes, beans, miscellaneous root crops, and double crops. Other residues include secondary agricultural processing residues, MSW, and fats and grasses.

TABLE 6

(in million dry tons per year)

PRODUCTION OF ESTER-BASED FUELS SUCH AS BIODIESEL FROM RENEWABLE STARTING MATERIALS

This application claims priority under 35 U.S.C. 119(e) to U.S. provisional application 60/968,222, filed Aug. 27, 2007, the contents of which are incorporated by reference in their entirety.

FIELD OF INVENTION

A method for the production of biodiesel and other ester-based fuels, such as jet fuel, from renewable starting materials such as whole plant oils is disclosed. In one embodiment, esterification of carboxylic acids recovered from pulping and saccharification of cellulosic material or other renewable starting material is accomplished via a gas sparged, slurry form of heterogeneous reactive distillation.

BACKGROUND

One area of interest for its ability to produce a net reduction in lifecycle carbon emissions comes in the form of alcohols produced by fermentation. Fermenting soluble sugars to produce ethanol or butanol is known in the art. While fermentation of soluble sugars may represent a way to energy self sufficiency for petroleum-challenged regions, the net lifecycle carbon dioxide emissions may actually exceed those of petroleum diesel and gasoline depending on the source of sugar and the method of its fermentation. For example, there is some debate as to whether ethanol produced from the fermentation of soluble sugars in corn grain consumes more carbon based energy than it produces. Not only is a great deal of fossil energy expended during the planting and harvesting of grain corn, but large amounts are required during the manufacture of ethanol—especially due to the water/alcohol separation and byproduct drying steps. Furthermore, carbon dioxide is a significant byproduct of fermentation itself. High soluble sugar content materials such as sugar beets and cane can increase net energy and carbon efficiency only to some degree.

One approach to achieving positive net energy production is to convert insoluble sugars such as cellulose from widely available lignocellulose material to soluble sugars that can be fermented. For example, the production of corn grain also yields a comparable amount of lignocellulosic material that is currently underutilized. The yield of grain ethanol from corn grain is about 29 wt %. The mass of corn stover to grain is roughly 1:1 and processes for recovering 20 wt % ethanol from stover have been commercialized. Converting the cellulose in stover to soluble sugar (a process known as saccharification or hydrolysis) consumes additional energy relative to that of simply tilling the stover back into the ground. However, the 70% increase in ethanol production compensates for the additional energy requirements causing the overall process to become respectably net energy productive.

The US Departments of Agriculture and Energy have estimated that the current availability of corn stover for use in ethanol production, without any change to current tillage or land use practices, to be about 75 million tons. If other lignocellulosic crop wastes are considered, the available cellulose from current agricultural practices is in excess of 190 million tons per year (Table 3). (U.S. Department of Agriculture and U.S. Department of Energy. BIOMASS AS FEEDSTOCK FOR A BIOENERGY AND BIOPRODUCTS INDUSTRY: THE TECHNICAL FEASIBILITY OF A BILLION-TON ANNUAL SUPPLY". April, 2005.) If no-till practices are adopted and crop yields increased, the amount of biomass available for fuel production can be increased to approximately 500 million tons per year (Table 4). Further expansion of available biomass to nearly a billion tons per year is achievable by increased farming of perennials such as switch grass (Table 5).

Forestry offers another source of cellulose for the production of ethanol. The US Departments of Agriculture and Energy have estimated that the current availability of cellulose from forest resources stands at 142 million tons per year and is expandable to 368 million tons per year (Table 6).

Underutilized cellulose from agriculture and forestry represents a resource for the production of net energy positive ethanol. Assuming the 1 billion tons per year or so that USDA and DOE estimate to be within reach along with a 20 wt % yield leads to over 60 billion gallons of ethanol production per year with a net reduction in $CO_2$ production. These resources can be realized only if the sugars locked in biomass in the form of insoluble cellulose can be separated from associated lignin and transformed into soluble sugar via saccharification/hydrolysis. Diverse technologies for accomplishing this separation exist at varying stages of investigation or commercialization. ("Costs Prohibit Cellulosics Use as Feedstock". C&EN, Apr. 12, 1976, pg. 12.)

Despite the investigation of ethanol as an alternative to petroleum to reduce carbon emissions, there remains a need for economically-viable energy alternatives such as plant and animal-derived ester-based fuels for controlling carbon dioxide emissions during the production of energy.

SUMMARY OF INVENTION

One object of the invention is to convert the fatty acid form of lipids that are liberated during the hydrolysis and saccharification of lignocellulosic material or other renewable starting material to ester based fuels. According to the invention, a process for the production of ester-based fuel from renewable starting material comprises: i) comminution of renewable starting material; ii) isolation of cellulose and other soluble and insoluble sugars, including isolation by hydrolysis and/or saccharification of the comminution product; iii) isolation of fatty acid and/or rosin acid; iv) addition of a C1-C8 alcohol to the fatty acid and/or rosin acid and esterification; and v) refining of the resulting ester to produce an ester-based fuel. According to one embodiment of the current invention, step iv of the invention is accomplished via the esterification method disclosed in U.S. Pat. No. 5,536,856 (Harrison et al.) which is utilized to esterify fatty and/or rosin acids with normal and branched alcohols with 1 to 8 carbons.

BRIEF DESCRIPTION OF THE DRAWINGS

FIG. 6 is an overall sequential block diagram of the embodiment of the invention as it applies to production of fuel esters from algae using alkali lyses.

FIGS. 7a and 7b are Table 1, which list potential oil yield data from lignocellulose materials.

FIG. 8 is Table 2, which categorizes several methods of concentrating micro algae.

FIG. 9 is Table 3, which is the available cellulose from current agricultural practices under certain conditions.

FIG. 10 is Table 4, which is the amount of biomass available for fuel production under the listed conditions.

FIG. 11 is Table 5, which is the available biomass achievable by increased farming of perennials such as switch grass.

DETAILED DESCRIPTION OF INVENTION

Figure 1:
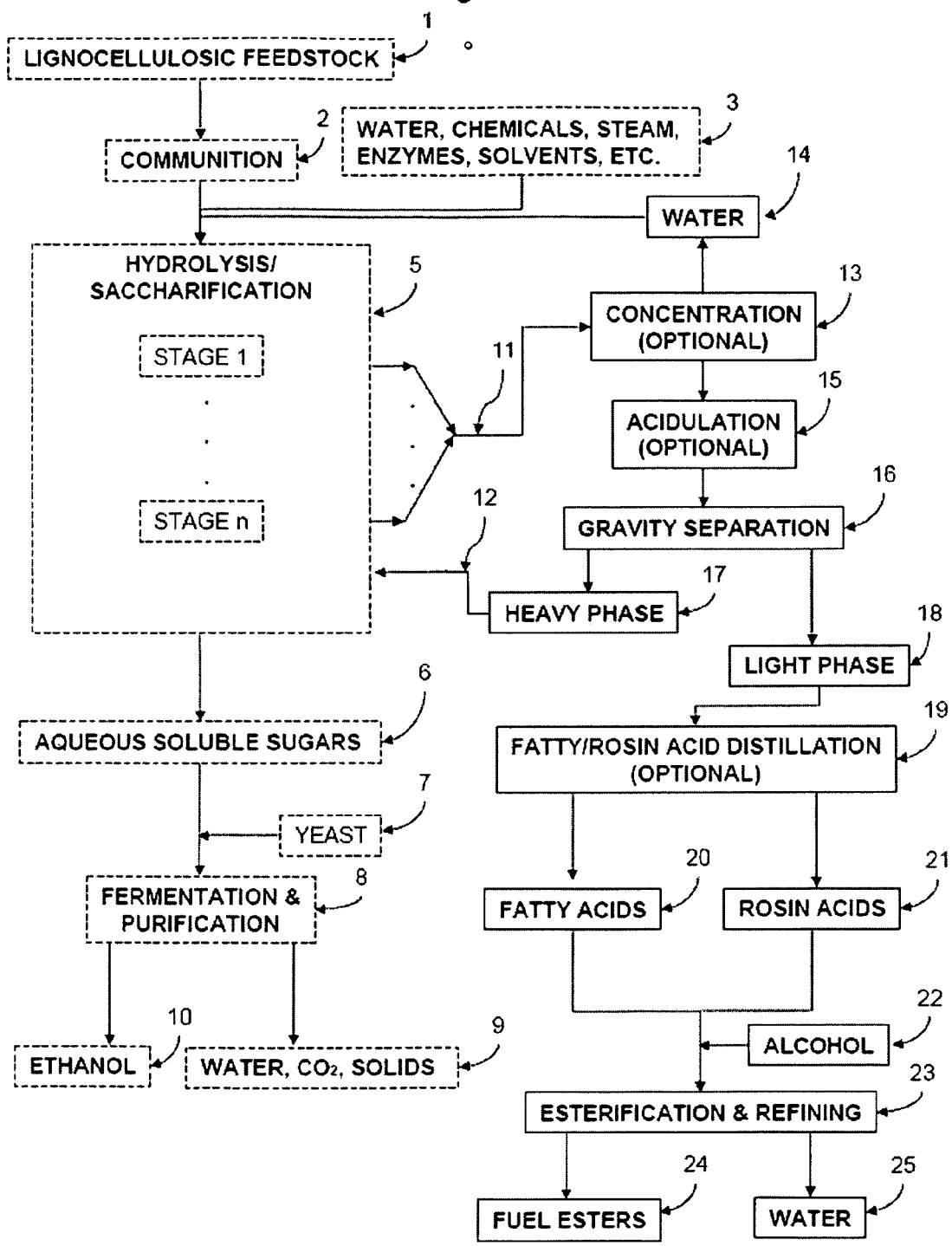
FIG. 1 is an overall sequential block diagram of the invention utilizing gravity settling.

Lipids are contained by all living cells as an energy store and are components of all living cell membranes. Typically, lipids produced for energy storage are in the form of glycerides while those found in cell membranes are in the form of phospholipids. In either case, the cellular destruction objective and the harsh conditions of the hydrolysis and saccharification technologies to achieve it also liberate cellular lipids in their glycerol- and phosphorous-free forms—i.e. as fatty acids. Such fatty acids can be converted into ester-based fuels. Producing energy from plant and animal-derived ester-based fuels represents one means of controlling carbon dioxide emissions during the production of energy due to reduction in net carbon emissions over the cycle of production and use associated with these materials. For example, soy biodiesel was shown to reduce net carbon emissions by 78% over petroleum diesel. (U.S. Department of Agriculture and U.S. Department of Energy. *Life Cycle Inventory of Biodiesel and Petroleum Diesel for Use in an Urban Bus*. May 1998.)

The present invention improves upon the prior art by increasing the feedstock pool available for the production of ester fuels by application of fatty and/or rosin acid technologies developed for Kraft processing. Utilizing an almost completely overlooked, enormous supply of fatty and/or rosin acids promises to greatly expand the renewable transportation fuel pool. The present invention also improves upon the prior art by supplying an esterification method that is more efficient, less polluting, and less capital intensive than transesterification processes used to convert glycerides to esters. The esterification process of the invention also greatly improves upon other wet chemical and heterogeneous esterification technologies by avoiding soap formation, overcoming equilibrium constraints, simplifying alcohol recovery, permitting online catalyst change out, and utilizing real-time dynamic and steady state optimization to manage optimization of catalyst usage, energy consumption, and feedstock costs.

Selection and Comminution of Renewable Starting Material

According to the invention, the first step in a process according to the invention involves selection of a renewable starting material as feedstock for the process. Selection of the renewable starting material involves an evaluation of cost of the starting material and estimation of yield of final product.

Materials destined for cellulosic ethanol production have been evaluated, and found to contain low relative concentrations of fatty acids. As a result, it is unlikely that many of these materials will ever be grown purely for that content. Rather, it will be their cellulose content that leads to byproduct fatty acid production. Relative to the amount of ethanol produced, the amount of fatty acid byproduct is actually quite significant. Assuming a typical yield of 20% ethanol and 2% fatty acid means that a minimum of 10% of an ethanol producer's high value products could be in the form of fatty acids.

Distillers dried grains with solubles (DDGS), the "other" product of corn grain fermentation, also contain a significant amount of lipids. Belyea et al. found 12 wt % "fat" on average and a maximum of 15.2 wt %. (Belyea, R. L., et al. "Composition of corn and distillers dried grains with solubles from dry grind ethanol processing". *Bioresource Technology*, 94 (2004), pp. 293-298; Belyea, R. L., et al. "Variability in the Nutritional Quality of Distillers Solubles". *Bioresource Technology*, 66 (1998) pp. 207-212.) However, because the grain corn contains ample soluble sugar, the process for liberating them is not harsh enough to render the fats in their fatty acid form. Rather, the fat from DDGS is predominantly in the glyceride form. The form of lipid content is included in the initial evaluation of the economic potential for a feedstock material.

According to the current invention, making use of DDGS for additional ethanol production rather than treating it as a byproduct would involve processing it in a way similar to other lignocellulosic materials. In doing this, the ethanol producer would gain additional ethanol yield and avoid handling and distribution costs involved in marketing DDGS. It would also result in conversion of the triglyceride lipids in DDGS to their fatty acid form thereby producing an ideal feedstock according to the esterification method of the invention.

One source of data useful in estimating potential yields of fatty acids from the hydrolysis of other lignocellulosic materials is laboratory experiments dedicated to the elucidation of the lipid composition of whole plant material. For example, Dien, B. S. et al. studied the composition of liquors produced by dilute acid pretreatment and enzymatic saccharification of alfalfa, reed canarygrass, and switchgrass. (Dien, B. S., et al. "Chemical composition and response to dilute-acid pretreatment and enzymatic saccharification of alfalfa, reed canarygrass, and switchgrass". *Biomass and Bioenergy*, 30 (2006), pp. 880-891.) They obtained maximum ether extracted fatty acid yields of 0.9 wt %, 2.2 wt %, and 1.6 wt % for alfalfa, reed canarygrass, and switchgrass respectively. Another source of potential oil yield data from lignocellulose materials comes in the form of livestock feedstuff analysis. Typical data where fat is expressed as "ether extractives" is given in Table 1.

Some possible starting materials are listed in Table 1, such as wheat straw, rice straw, rapeseed, rapeseed plant, field pennycress, Jatropha, mustard, flax, sunflower, canola, palm, hemp, cotton plant, sunflower plant, peanut, tobacco, sugarcane, sugarbeet, potatoes, sorghum, barley, oats, beans, hardwood, softwood, pine wood, forest products, wood residues, coconut copra, alfalfa, canarygrass, switchgrass, soy plant, soy bean, corn, corn grain, corn stover, and any other starting materials, as desired.

In one economically important field, the yield of fatty acids from Kraft processing of pine wood is known to be in the range of 15-20 kg/ton of dry wood. Even with Kraft pulping there is room for improvement. Only approximately 45% of CTO (crude tall oil) available in the pine tree is recovered. The rest is lost during woodyard operations (20%), pulping (15%), black liquor recovery (15%), and acidulation (5%). Several processing changes have been proposed to improve this yield. For instance, woodyard operations have become more efficient, with a turnover of one week, as opposed to two months, when these numbers were recorded. This has compensated for CTO losses that resulted from an increased use of hardwood. CTO losses due to soap adsorption on the pulp can be reduced, too. In a 1400 t/d pulp mill, about 25 t/d of soap is left on the pulp. Much of this soap can be recovered by adding N,N-dimethyl amides of tall oil fatty acids to the wash water of the rotary drum vacuum filter in the third and final pulp washer stage. Also, the addition of 6-7 grams of propyl stearic amide to the wash system per ton of pulp has been reported to increase tall oil soap yields significantly. (Huibers, D. (Union Camp Corporation). *Tall Oil*. Kirk-Othmer Encyclopedia, John Wiley and Sons, 1996.)

Because most other hydrolysis processes and lignocellulosic sources are experimental, thinly commercialized, and lacking in optimization, it is rare to find literature dedicated to the concept of the recovery of fatty and/or rosin acids as byproducts from them. This is somewhat surprising given the potential 1.5-2.0 wt % yield of fatty acids implied by pine wood. Simple translation of this yield to the current unutilized portion of agricultural waste lignocellulose is equivalent to approximately 1 billion gallons pr year of ester fuels. Furthermore, it is well known that certain crop wastes have several times the potential fatty acid yield of pine wood.

As an alternative to crop waste, single celled plants such as bacteria, algae, and yeasts offer another underutilized source of lipids from which fatty acids can be recovered in much the same way as with lignocellulosic materials. Algae, in particular, produce and utilize lipids in much the same way as plants. Like plants, they have tough outer coatings that contain phospholipid chains. They also produce triglycerides as an energy store. Also like plants, they can be readily grown in enormous, outdoor farms. While yeast and bacteria are used commercially to produce a variety of fine chemicals such as alcohols, acetone, proteins, and insulin, use of algae to produce large quantities of lipids is a new industry.

Algae come in both prokaryotic (bacteria like) and eukaryotic (plant and animal like) forms. What distinguishes algae is that they are one celled or multicellular organisms capable of performing photosynthesis yet lacking in leaves, roots, flowers, seeds, and other organs. Prokaryotic cyanobacteria, such as spirulina or blue-green algae, are considered to be half bacteria and half algae. Eukaryotic algae have decidedly plant-like cell structures and can even assemble into structures such as kelp, also known as brown algae, and seaweed, also known as green algae, that resemble whole plants. The different levels of organization of algae cells are as follows:

- Colonial—small, regular groups of motile cells
- Capsoid—individual non-motile cells embedded in mucilage
- Coccoid—individual non-motile cells with cell walls
- Palmelloid—non-motile cells embedded in mucilage
- Filamentous—a string of non-motile cells connected together, sometimes branching
- Parenchymatous—cells forming a thallus with partial differentiation of tissues Algae tend to produce lipids with high degrees of unsaturation. (Evans, R. W. et al. "LIPID COMPOSITION OF HALOTOLERANT ALGAE, DUNALIELLA PARVA LERCHE AND DUNALIELLA TERTIOLECTA". Biochemica et Biophysica Acta, 7 12 (1982), pp. 186-195.) Most algae are strictly autophototropic, deriving energy from photosynthesis. Some forms are mixotropic and can derive energy from both photosynthesis and uptake of carbon molecules. Commercial growing of Algae is accomplished in systems that provide water for suspending the algae, light, nutrients, and carbon dioxide. These so called photobioreactors take on a variety of forms. (For example, see Rorrer, G., Mullikin, R. "Modeling and simulation of a tubular recycle photobioreactor for macroalgal cell suspension cultures". *Chemical Engineering Science* 54 (1999) pp. 3153-3162.)

According to the current invention, algal paste concentrates are lysed with alkali and heat to saponify the fats and lipids contained within the cells. The saponified fatty acids are recovered by phase separation (skimming) from the cooking liquor and acidulated to yield free fatty acids. These fatty acids are then esterified according to the esterification method of the invention. Also according to the current invention, algal paste concentrates are lysed with acids and the fatty acids are recovered via phase separation. These fatty acids are then esterified according to the esterification method of the invention.

Delignification in the Production of Ester-Based Fuels

Once a renewable starting material is chosen as the feedstock for a process according to the invention, the starting material is processed to separate out the fatty acid. For lignocellulosic starting materials, processing includes removal of the lignocellulose. This processing step may be informed by processes used in ethanol production and paper pulping.

The goal of freeing cellulose from its lignin matrix (i.e. pulping) is common to both ethanol production and paper making. Large-scale ethanol production seeks to further transform liberated cellulose into water-soluble sugars via staged operations. These goals are similar to that of paper making and recovery of fibers from lignocellulosic materials. The main difference between paper making and ethanol production has to do with the final disposition of cellulose. With paper making, the goal is to recover as high of a yield of clean, i.e. lignin-free, cellulose fibers as possible. With ethanol production, lignin-free cellulose is an intermediary material which must be further transformed into soluble sugars such as glucose. This extra step is known as saccharification or hydrolysis.

The overall process from lignocellulosic fiber to soluble sugar usually follows a sequence beginning with some form of mechanical comminution, followed by chemical and/or hydrothermal pulping and delignification (hydrolysis), and followed by further saccharification. While they differ in terms of the specific pulping, delignification, and saccharification methods, the harsh conditions used in these processes all liberate the fats, and other potential sources of ester-based biofuels contained in plant matter, as carboxylic acids rather than glycerides.

It is possible to group technologies into classes. Each class can be used alone or in combination with another class to effect the transformation of the cellulose in lignocellulose material to soluble sugar as part of the process of separating out fatty acids:

1. Alkaline Solution Pulping (Kraft)
2. Dilute Acid Pulping
3. Concentrated Acid Pulping
4. Organic Solvent Pulping
5. Hydrothermal Pulping
6. Ammonia, or Carbon Dioxide Pulping
7. Wet Oxidation Pulping
8. Enzymatic Hydrolysis
9. Bacterial Digestion A commercial process for pulping of biomass which already produces a billion pounds per year of carboxylic acids suitable for use in the present invention is known as the Kraft process. Kraft processing is a major source of paper pulp. Kraft processors normally utilize some form of mechanical reduction of plant mass (wood) such as grinding, followed by treatment of the plant mass with heat and a solution of water, strong base, and $Na_2S$ (also known as white liquor) in order to separate cellulose from lignin. (Sell, J. N., Norman, J. C., "Chemical and Physical Properties of High-Yield Alkaline Sulfite Green Liquor". *Ind. Eng. Chem. Res.* 32 (1993), pp. 2794-2199.) During Kraft pulping, the resin and fatty acids in the wood are saponified into soaps. The solution of these soaps along with lignin is known as black liquor. (Wagner, C. L. "Alkali Recovery from Pulp Liquors by a Chemical Engineering Process". *Industrial and Engineering Chemistry, Vol. 22*, No. 2, (February 1930), pp. 122-127.)

Black liquor is separated from the desired cellulose fiber by filtration. Acidifying black liquor with sulfuric acids causes the fatty and/or rosin acid soaps contained in black liquor to precipitate out as a separate, oily phase. This oily phase is then recovered by physical means, such as skimming, as "tall oil". Tall oil can be further processed by distillation to produce pure rosin acid, fatty acid, sterol, and ester products. (Huibers, D. (Union Camp Corporation). *Tall Oil*. Kirk-Othmer Encyclopedia, John Wiley and Sons, 1996.) The rosin and fatty acids thus produced from pine wood feedstock make excellent feedstocks for the esterification method of the present invention due to their high degree of unsaturation. High unsaturation leads to ester fuels with exceptional low temperature properties.

While fatty and/or rosin acids produced from the Kraft process are suitable, other pulping and delignification processes may also yield carboxylic acids suitable for the production of biofuel esters. These methods may be classified as mechanical, chemical, semi-chemical, hydrothermal, or enzymatic processes. (Kadla, J. and Qizhou, Dai, (University of British Columbia). Pulp. Kirk-Othmer Encyclopedia, John Wiley and Sons, Vol. 21, 2006.; Mabee, W. E., et al. "Updates on Softwood-to-Ethanol Process Development". *Applied Biochemistry and Biotechnology*, Vol. 129-132 (2006), pp. 55-70.; Mohanty, B. "Technology, Energy Efficiency and Environmental Externalities in the Pulp and Paper Industry". Asian Institute of Technology, 1997.)

Alkaline solution pulping is the most prevalent today. Kraft or Sulfite pulping accounts for most alkaline pulping performed commercially. Soda, and Soda-anthraquinone are other examples of water based, alkaline pulping. (Sun, R. C., et al. "Structural and physico-chemical characterization of lignins solubilized during alkaline peroxide treatment of barley straw". *European Polymer Journal*, 38 (2002), pp. 1399-1407.) Xylan Inc. discloses an alkaline pulping process that utilizes extrusion and hydrogen peroxide. (Dale, M. C. "The Xylan Delignification Process for Biomass Conversion to Ethanol." Paper Presented at the 17$^{th}$ Annual Biotechnology for Fuels and Chemicals Symposium, Vail, Colo., May, 1995.) Aronovsky and Gortner published a series of articles in the 1930's detailing various alkaline and acidic "Cooking Processes". (Aronovsky, S. I., Gortner, R. A. "The Cooking Process I—Role of Water in Cooking Wood". *Industrial and Engineering Chemistry*, Vol 22, No. 3 (March 1930), pp. 264-274.)

Pulping with dilute acid solutions is practiced. (Hakansson, H., Ahlgren, P., "Acid hydrolysis of some industrial pulps: effect of hydrolysis conditions and raw material". *Cellulose*, Vol. 12 (2005), pp. 177-183.) U.S. Pat. No. 5,705,369 discloses a process whereby soluble sugars are recovered by passing a weakly acidic solution through solid cellulosic material and recovering the sugars from the filtrate. U.S. Pat. No. 6,228,177 (Torget) discloses a process whereby dilute acid is used in several stages for the hydrolysis and fractionation of biomass. U.S. Pat. No. 6,423,145 (Nguyen et al) discloses a process whereby biomass hydrolysis is accomplished with dilute acid and a metal salt catalyst. Alternatively, aqueous or supercritical $CO_2$ may be used. See, for example, U.S. Pat. No. 2,232,331, which discloses a process where $CO_2$ is introduced to soap solutions at 50 atmospheres both with and without various solvents either miscible or immiscible in water. See also U.S. Pat. No. 4,495,095, which employs multiple rounds of contact between supercritical $CO_2$ and tall oil solution.

Pulping with concentrated acid solutions is also practiced. (Harris, E. E. "Wood Saccharification." In Advances in Carbohydrate Chemistry, Vol 4, Academic Press, New York, 1949, pp 153-188.) U.S. Pat. Nos. 5,562,777 and 5,580,389 (Farone & Cuzens) disclose a strong acid hydrolysis method of obtaining soluble sugars from rice straw and other lignocellulosic material. In this process, soluble sugars are recovered from pulping liquor by adsorption. The sugar free liquor is then recycled for use in the hydrolysis steps.

Organic solvents are also employed along with these more conventional processes. Examples include ASAM (alkaline-sulfite-AQ-methanol), OrganoCell (soda-AQ-methanol), or a nonconventional process, e.g., Alcell (acid-catalyzed ALcohol-CELLulose), Acetosolv and Acetocell (acetic acid pulping), MILOX (peroxyformic acid). (Goncalves, A. R., et al. "Integrated Processes for Use of Pulps and Lignins Obtained from Sugarcane Bagasse and Straw". *Applied Biochemistry and Biotechnology*, Vol. 121-124 (2005), pp. 821-826; Pan, X., et al. "Biorefining of Softwoods Using Ethanol Organosolv Pulping: Preliminary Evaluation of Process Streams for Manufacture of Fuel-Grade Ethanol and Co-Products". *Biotechnology and Bioengineering*, Vol. 90, No. 4, (May 20, 2005), pp. 473-481; Aronovsky, S. I., Lynch, D. F. J. "Pulping Bagasse with Alcoholic Nitric Acid Pulp Yields and Characteristics". *Industrial and Engineering Chemistry*, Vol. 30, No. 7 (July 1938), pp. 790-795.) The use of ethylene glycol has been studied. (Rezzoug, S., Capart, R. "Solvolysis and Hydrotreatment of Wood to Provide Fuel". *Biomass and Bioenergy*, Vol. 11, No. 4 (1996), pp. 343-352.; Rezzoug, S., Capart, R. "Liquefaction of wood in two successive steps: solvolysis in ethylene-glycol and catalytic hydrotreatment". *Applied Energy*, 72 (2002), pp. 631-644; Ammar, S., et al. "Simple Mathematical Model for the Solvolysis of Cylindrical Pine-Wood Samples". *Applied Energy*, 48 (1994), pp. 137-148; Thring, R. W. "Recovery of a Solvolytic Lignin: Effects of Spent Liquor/Acid Volume Ratio, Acid Concentration and Temperature". *Biomass*, 23 (1990), pp. 289-305; Bouvier, J. M., et al. "Wood Liquefaction an Overview". *Applied Energy*, 30 (1988), pp. 85-98.)

A hydrothermal process known as steam explosion is considered a potential low cost pulping technique. (Garrote, G., et al. "Hydrothermal Processing of Lignocellulosic Materials." *Holz als Roh- and Werkstoff* 57 (1999) pp. 191-202; Bonini, C., D'Auria. M. "Degradation and recovery of fine chemicals through singlet oxygen treatment of lignin". *Industrial Crops and Products*. 20 (2004), pp. 243-259; Garrote, G., et al. "Autohydrolysis of agricultural residues: Study of reaction byproducts". *Bioresource Technology*, 98 (2007), pp. 1951-1957; Shahbazi, A., et al. "Application of Sequential Aqueous Steam Treatments to the Fractionation of Softwood". *Applied Biochemistry and Biotechnology*, Vol. 121-124 (2005), pp. 973-987; Marchessault, R. H., et al. "Characterization of aspen exploded wood lignin". *Can. J. Chem.*, Vol. 60 (1982), pp. 2372-2382.) It involves treatment of wood or other fiber with high pressure, saturated steam for a period of time followed by sudden pressure letdown. As a result of the sudden letdown, the steam impregnated fiber cells expand rapidly and "explode" releasing there chemical constituents. Only a small amount of lignin becomes water soluble during steam explosion. Post treatment with 0.1M aqueous alkali solution or organic solvents is required to dissolve water insoluble lignin. Variations on the concept where $CO_2$ or $NH_3$ are used in place of steam are also practiced. (Sun, Y., Cheng, J. "Hydrolysis of lignocellulosic materials for ethanol production: a review". *Bioresource Technology*. 83 (2002) pp. 1-11; Mes-Hartree, M., et al. "Comparison of steam and ammonia pretreatment for enzymatic hydrolysis of cellulose". *Appl Microbiol Biotechnol* (1988) 29, pp. 462-468; Garrote, G., et al. "Autohydrolysis of corncob: study of non-isothermal operation for xylooligosaccharide production".

*Journal of Food Engineering*, 52 (2002), pp. 211-218; Kim, T. H., et al. "Pretreatment of corn stover by aqueous ammonia". *Bioresource Technology*, 90 (2003), pp. 39-47.)

Hydrothermal treatment in combination with oxygen in a process known as "Wet-Oxidation" is also receiving attention. Variations on this process include the use of catalytic amounts of metal salts such as ferric or cupric sulfate, alkaline conditions, and thermophilic, anaerobic bacteria. (McGinnis, G. D., et al. "Biomass Pretreatment with Water and High-pressure Oxygen. The Wet-Oxidation Process". *Ind. Eng. Chem. Prod. Res. Dev.* 1983, 22, pp. 352-357; Klinke, H. B., et al. "Characterization of the Degradation Products from Alkaline Wet-Oxidation of Wheat Straw". *Bioresource Technology*, 82 (2002), pp. 15-26; Sun, R. C., et al. "Chemical composition of lipophilic extractives released during the hot water treatment of wheat straw". *Bioresource Technology*, 88 (2003) pp. 95-101; Ahring, B. K., et al. "PRETREATMENT OF WHEAT STRAW AND CONVERSION OF XYLOSE AND XYLAN TO ETHANOL BY THERMOPHILIC ANAEROBIC BACTERIA". *Bioresource Technology*, 58 (1996), 107-113; Minowa, T. et al. "Liquefaction of Cellulose in Hot Compressed Water Using Sodium Carbonate: Products Distribution at Different Reaction Temperatures". *Journal of Chemical Engineering of Japan*, Vol. 30, No. 1 (1997), pp. 186-190; Karagoz, S., et al. "Catalytic hydrothermal treatment of pine wood biomass: effect of RbOH and CsOH on product distribution". *J Chem Technol Biotechnol*, 80 (2005), pp. 1097-1102; McGinnis, G. D., et al. "Conversion of Biomass into Chemicals with High-Temperature Wet Oxidation". *Ind. Eng. Chem. Prod. Res. Dev.* 1983, 22, pp. 633-636.)

Enzymatic hydrolysis has also received a good deal of attention lately since it offers the potential of lower utility consumption over acid or alkaline hydrolysis. (Akin, D. E., et al. "Corn Stover Fractions and Bioenergy". *Applied Biochemistry and Biotechnology*, Vol. 129-132 (2006), pp. 104-116.) Cellulases are usually a mixture of several enzymes. At least three major groups of cellulases are involved in the hydrolysis process: (1) endoglucanase (EG, endo-1,4-D-glucanohydrolase, or EC 3.2.1.4.) which attacks regions of low crystallinity in the cellulose fiber, creating free chain-ends; (2) exoglucanase or cellobiohydrolase (CBH, 1,4-b-D-glucan cellobiohydrolase, or EC 3.2.1.91.) which degrades the molecule further by removing cellobiose units from the free chain-ends; (3) b-glucosidase (EC 3.2.1.21) which hydrolyzes cellobiose to produce glucose. In addition to the three major groups of cellulase enzymes, there are also a number of ancillary enzymes that attack hemicellulose, such as glucuronidase, acetylesterase, xylanase, b-xylosidase, galactomannanase and glucomannanase. During the enzymatic hydrolysis, cellulose is degraded by the cellulases to reducing sugars that can be fermented by yeasts or bacteria to ethanol. Enzymatic hydrolysis has also been used in conjunction with steam (hydrothermal) treatment. (Palmarola-Adrados, B., et al. "Combined Steam Pretreatment and Enzymatic Hydrolysis of Starch-Free Wheat Fibers". *Applied Biochemistry and Biotechnology*, Vol. 113-116, 2004, pp. 989-1002; Ohgren, K., et al. "Effect of hemicellulose and lignin removal on enzymatic hydrolysis of steam pretreated corn stover". *Bioresource Technology*, 98 (2007), pp. 2503-2510.) It along with dilute acid pretreatment have also been studied. (Dien, B. S., et al. "Chemical composition and response to dilute-acid pretreatment and enzymatic saccharification of alfalfa, reed canarygrass, and switchgrass". *Biomass and Bioenergy*, 30 (2006), pp. 880-891.) U.S. Pat. Nos. 3,990,994 (Gauss et al.) and 3,990,995 (Huff and Yata) disclose cellulase-based hydrolysis processes.

The use of bacteria itself for digestion of lignocellulose is known for coconut shells. The process designed specifically to produce oil from dried coconut shells, also known as copra, is described by Beckman. He describes a "Bacterial Oil Recovery Process" as applied to the dried shell of the coconut. (Beckman, J. W. "Recovery of Vegetable Oils and Fats by a Bacterial Process". *Industrial and Engineering Chemistry*, Vol. 22, No. 2 (February 1930), pp. 117-118.) U.S. Pat. No. 1,698,294 (Beckman) describes this process in more detail.

When algae are chosen as the renewable starting material instead of lignocellulosic material, the processing requires concentration of the algae. The method of algae harvesting depends on the level of organization. Seaweeds and kelp can simply be "picked", for example, while micro algae such as diatoms, green, golden, and blue green algae must somehow be concentrated from their dilute (typically <500 mg/L), water dispersed form to something in the range of 15% solids. Methods such as centrifugation, cross-flow membrane filtration, and flocculation are practiced. (Tilton, R. C., Dixon, J. K. "THE FLOCCULATION OF ALGAE WITH SYNTHETIC POLYMERIC FLOCCULANTS". *Water Research* 1972. Vol. 6, pp. 155-164; Rossignol, N. "Membrane technology for the continuous separation microalgae:culture medium: compared performances of cross-flow microfiltration and ultrafiltration". *Aquacultural Engineering* 20 (1999), pp. 191-208; Fish, N. M., Lilly, M. D. "The Interactions between Fermentation and Protein Recovery". *Biotechnology*, July, 1984, pp. 623-627.) Table 2 categorizes several methods of concentrating micro algae.

Once the cells are sufficiently concentrated, it becomes necessary to "disrupt", rupture, or "homogenize" them so that compounds of interest are released for recovery. When the compound of interest is a protein, enzyme, or other delicate compound, mechanical destruction methods and equipment are employed. (Chisti, Y., Moo-Young, M. "Disruption of microbial cells for intracellular products". *Enzyme Microb. Technol*. April, 1986, vol. 8, 194-204. Hedenskog, G., Mogren, H. "Some Methods for Processing of Single-Cell Protein". BIOTECHNOLOGY AND BIOENGINEERING, 15, pp. 129-142 (1973). Molina Grima, E., et al. "Recovery of microalgal biomass and metabolites: process options and economics". *Biotechnology Advances*, 20 (2003), pp. 491-515.) Mechanical methods are characterized as employing solid or liquid shear. Examples of solid shear equipment include the bead mill (Shutte, H. et al. "Experiences with a 20 liter industrial bead mill for the disruption of microorganisms". *Enzyme Microb. Technol.*, March 1983, Vol. 5, pp. 143-148. Currie, J. A., et al. "Release of Protein from Bakers' Yeast (*Saccharomyces cerevisiae*) by Disruption in an Industrial Agitator Mill". BIOTECHNOLOGY AND BIOENGINEEKING, 14 (1972), pp. 725-736.), freeze press (Magnusson, K. E., Edebo, L. "Large-Scale Disintegration of Microorganisms by Freeze-Pressing". BIOTECHNOLOGY AND BIOENGINEERING, 18, (1976), pp. 975-986.), Dyno-Mill (Marffy, F., Kula, M. "Enzyme Yields from Cells of Brewer's Yeast Disrupted by Treatment in a Horizontal Disintegrator". BIOTECHNOLOGY AND BIOENGINEERING, 16 (1974), pp. 623-634; Mogren, H. et al. "Mechanical Disintegration of Microorganisms in an Industrial Homogenizer". BIOTECHNOLOGY AND BIOENGINEERING, 16 (1974), pp. 261-274.), and the Hughes press (Scully, D. B. "Thermodynamics and Rheology of the Hughes Press". *BIOTECHNOLOGY AND BIOENGINEERING*, 16 (1974), pp. 675-687). Examples of liquid shear equipment, or homogenizers, include the Manton-Gaulin APV homogenizer. Doulah, M. S. et al. "A Hydrodynamic Mechanism for the Disintegration of *Saccharomyces cerevesiae* in an Industrial Homogenizer". *BIOTECHNOLOGY AND BIOENGINEERING*, 17 (1975), pp. 845-858. Mosqueira, F. G. "Characteristics of Mechanically Disrupted Bakers' Yeast in Relation to its Separation in Industrial Centrifuges". *Biotechnology and Bioengineering*, 23 (1981), pp. 335-343. Whitworth, D. A. et al. "Hydrocarbon Fermentation: Protein and Enzyme Solubilization from *C. lipolytica* Using an Industrial Homogenizer", 16 (1974), pp. 1399-1406.) Lipids liberated by mechanical disruption of cells tend to be mainly in their triglyceride form. That is to say, a lipid fraction isolate from the mechanical destruction of algal cells will have a small ratio of acid number to saponification value.

As with lignocellulose pulping, the use of chemicals alone or in combination with mechanical methods can improve disintegration of algae. It is often suggested to simply dry, crush, and extract oil from algae using hexane much in the same way that oil is recovered from soybeans. (Xu, H. et al. "High quality biodiesel production from a microalga *Chlorella* protothecoides by heterotrophic growth in fermenters". *Journal of Biotechnology*, 126 (2006), pp. 499-507. Miao, X., Wu, Q. "Biodiesel production from heterotrophic microalgal oil". *Bioresource Technology*, 97 (2006), pp. 841-846.) Lysis, as chemical disruption is known, can be accomplished by methods similar to Kraft pulping (Minowa, T. "Oil production from algal cells of *Dunaliella tertiolecta* by direct thermochemical liquefaction". *Fuel* Vol. 74 No. 12, (1995), pp. 1735-1738.) as well as enzymatically. While chemical lysis with alkali tends to damage sensitive compounds, it is very effective in obtaining higher yields of fatty acids in their soap form. Furthermore, alkali lysing lends itself very well to large scale production. Concentrated algae paste is simply subjected to alkali and heat much as wood fiber is treated during the Kraft process. The resulting fatty acid soaps float to the top of the water layer along with other organics forming an organic layer which is 30-40% fatty acids. This layer can be skimmed and acidulated to affect separation of the fatty acids as an oil layer. (Zhu, Z., et al, "Extraction of lipids from *Mortierella alpina* and enrichment of arachidonic acid from the fungal lipids". Bioresource Technology, 84 (2002), pp. 93-95. Rezanka, T. "DETERMINATION OF FATTY ACIDS IN ALGAE BY CAPILLARY GAS CHROMATOGRAPHY-MASS SPECTROMETRY". *Journal of Chromatography*, 268 (1983), pp. 71-78. Minowa, T., Gillan, F. T., Dunstan, G. A., et al., Orcutt, D. M., Volkman, J. K., et al.) The process of saponification followed by acidulation closely resembles the way in which soapstock from palm or soybean oil is created and then acidulated. It is also similar to how tall oil is recovered. The lipids thus recovered will have nearly equal saponification and acid number values.

Isolation of Fatty Acids

Once a conversion of cellulose to soluble sugar has been accomplished, the recovery of fatty and rosin acids from the various stages can proceed. While fatty acids, and sometimes rosin acids, can be liberated as a result of the hydrolysis/saccharification of lignocellulosic material, the optimum method for and optimum stage in the process for their recovery may differ. Because lipids are bound in plant cell structures along with lignin, it is possible that the point of highest concentration of lipids in a given hydrolysis process will be at a point when the cellulose fraction is mostly lignin free.

While the various hydrolysis/saccharification processes and combinations thereof all liberate fatty and/or rosin acids, concentrations of these byproducts and the form they take at different stages in the process may vary. It is possible to propose taking advantage of the solubility behavior of fatty and rosin acids in their acid form to aid in isolation. Therefore, according to the current invention, phase separation, either in terms of gravity settling and/or rosin acids or liquid-liquid extraction, is proposed as the means of recovery of fatty and rosin acids from hydrolysis/saccharification liquors. According to the current invention, liquid-liquid extraction can be performed in batch or continuous fashion. According to the current invention, the extractive solvent used in liquid-liquid extractions is chosen in order to optimize competing objectives of low solubility in pulping liquor, high affinity for fatty and/or rosin acids, high density difference between pulping liquor and loaded solvent, and ease and energy efficiency of solvent recovery.

Depending on whether the hydrolysis process involves alkaline or acidic conditions, the form of the lipids at this point will either be fatty acids or fatty acid soaps. Fatty acids form soaps with the cation from alkaline salts. In this form, fatty acids have enhanced water solubility. Furthermore, they may serve to help render lignin more water soluble and hence easier to separate from cellulose. When conditions are acidic, the soap-free fatty acid form of lipids dominates. In this form, the fatty and/or rosin acids of interest are not water soluble.

This lack of water solubility for the fatty acid form of lipids provides the most viable means for their recovery separate from high concentration lignin liquors, cellulose fibers, and sugar solutions. Depending on conditions, fatty and/or rosin acids will either form a separate liquid phase that can be "skimmed" from aqueous or organic liquors or be readily extracted there from using a water insoluble, organic solvent.

How fatty and/or rosin acids are recovered from Kraft processes provides a framework for how they can be covered by hydrolysis/saccharification processes. The Kraft pulping process yields strong cellulose fibers by digesting pinewood chips for about two hours with an aqueous mixture of sodium hydroxide and sodium sulfide at 165-175° C. under pressure. During pulping, the 2-3% resin and fatty acids that naturally occur in resinous wood are saponified. After filtration of the fibers, pulping black liquor is concentrated by multistage evaporation prior to feeding to a furnace for the recovery of the sodium salts and energy values. Black liquor soap consists of the sodium salts of the resin and fatty acids with small amounts of unsaponifiables. The soap is most easily separated from the black liquor by skimming at an intermediate stage, when the black liquor is evaporated to 25% solids. At this solids level, the soap rises in the skimmer at a rate of 0.76 m/h. At higher solids concentrations, the tall oil soap is less soluble, but higher viscosity lowers the soap rise rate and increases the necessary residence times in the soap skimmer beyond 3-4 hours. The time required for soap recovery can be reduced by installing baffles, by the use of chemical flocculants, and by air injection into the suction side of the soap skimmer feed pump. Soap density is controlled by the rate of air injection. Optimum results (70% skimmer efficiency) are obtained at a soap density of 0.84 kg/L (7 lb/gal). This soap has a minimum residual black liquor content of 15%. (Huibers, D)

In essence, Kraft pulping is a form of alkaline hydrolysis that is halted the point at which the yield of insoluble cellulose fiber and its lignin content (expressed as "kappa" number) reach an optimum value. Continuing the cooking process for longer periods of time would result in both higher lignin removal from and conversion to soluble sugar of cellulose fibers. In fact, certain variations of alkaline hydrolysis/saccharification essentially use Kraft pulping as a "pretreatment" step to be followed by either more alkaline or enzymatic cooking With these processes, the tall oil recovery methods discussed above are directly applicable.

Kraft pulping makes up approximately 95% of the pulping capacity in the US. The lack of recovery of fatty and/or rosin acids from the next most practiced pulping method, Sulfite pulping, is instructive as to the state of recovery of fatty and/or rosin acids from non-Kraft pulping processes. Pearl and McCoy (1960) demonstrated that fatty and/or rosin acids can be recovered from sulfite pulping liquors via ether extraction. However, the presence of these materials in extracts was somewhat of a surprise to them and led them to hypothesize that more could be recovered from the mother liquor. (Pearl, I. A., McCoy, P. F. "Studies on the Chemistry of Aspenwood. VIII.' An Investigation of the Neutral Extractives off Commercial Aspen Spent Sulfite Liquors". *J. Org. Chem., Vol. 26*, pp. 550-552.)

In general, it is proposed that fatty acids, and rosin acids in the case of some plant materials, exist in pulping liquors and can be recovered. Depending on the type of and stage in a given process, these carboxylic acids will either be in soap or acid form. They will exist, at least partly, in soap form when conditions are alkaline and in fatty acid form, at least partly, when under neutral or acidic conditions. When they are in acid form, they will form a separate phase from an aqueous or polar organic liquor. When they are in soap form, they will tend to be dissolved in the aqueous liquor. As in Kraft processing, concentrating a given liquor will improve the ability to recover fatty and/or rosin acids whether in soap or acid form. According to the current invention, evaporative concentration of fatty and/or rosin acid containing liquors may be performed prior to gravity settling or liquid-liquid extraction in order to improve recovery.

When fatty and/or rosin acids are concentrated enough and in insoluble form such that they form a separate phase, they can be removed by physical separation. This can involve simply allowing the liquids to "settle" and then skimming off the top oil layer or removing the bottom liquor layer. Various vessels designs have been used over the years to improve separation efficiency and throughput. API and Lamella settlers are examples of the culmination of such art. U.S. Pat. No. 3,562,096 (Tourtellotte) discloses the use of continuous centrifugation to affect the physical separation between fatty acid and resin "soaps" and cooking liquor.

Liquid-liquid extraction of fatty and/or rosin acids from aqueous or polar organic liquors is a second method available for their recovery. Extraction can be performed at various stages in a given hydrolysis/saccharification process. It can be accomplished in both batch and continuous fashion using any of a number of water insoluble organic solvents such as petroleum ether, normal, cyclo, and iso-paraffins such as n-hexane and n-octane, alpha-olefins, petroleum naphtha, diesel, benzene, etc. The choice of solvent involves considerations such as density difference between the solvent when loaded with fatty and/or rosin acids and the depleted pulping liquor, partitioning coefficient between fatty and/or rosin acids and the solvent and liquor, and ease of post-separation from the fatty and/or rosin acids. Post-separation methods include distillation and membrane separation. However, while membrane separation can impart energy efficiencies related to that lost from cooling distilled solvent, it is most likely that distillation will be required even if membrane separation is used.

Batch extraction is normally performed by first blending a previously optimized amount of the chosen solvent, either fresh or recovered, with a previously optimized amount of pulping liquor and then agitating. After some optimal time, agitation is ceased and the liquids are allowed to separate into two or more phases. Often, a middle phase (known as a "rag layer") will form between both desirable and undesirable extracts and liquors. The upper phase will now contain the fatty and/or rosin acids dissolved in the solvent. The bottom phase is decanted either up to or past any rag layer. If the rag layer is recovered, it is most likely sent to separate storage for further processing or recycle. Once the upper phase is all that remains in the vessel, it is subjected to either batch or continuous distillation. Batch distillation can be performed by simply applying heat to the extraction vessel and refluxing some of the vapor back into the vessel via a packed or trayed column or it can be accomplished in a separate vessel.

Continuous extraction is normally performed using a vertical trayed and/or packed column. Fresh and/or recovered solvent can be fed to a location just above the bottom of the column and aqueous or polar organic liquor is similarly fed to a location just below the top of the column. Sufficient column length both below the solvent feed and above the liquor feed is provided to permit disengagement of the two solvents by settling. In this way, liquid drawn from the very top of the column can be liquor free and liquor drawn from the very bottom of the column can be solvent free. The trays and/or packing serve to increase interfacial area between the two liquid phases as well as to create an equilibrium staged, counter current operation.

The fatty and resin acid depleted liquor from the bottom of the column should be as solvent free as possible to enable further processing or disposal in the normal fashion. Solvent choice plays an important role in making that happen. The solvent should not be very soluble in the bottom liquor or else its loss will contribute to operating cost both and could effect downstream processing.

According to the current invention, the extractive solvent may be recovered by separating it from product fatty and/or rosin acids by batch or continuous distillation. The fatty and resin acid rich solvent from the very top of the column can be fed to continuous or batch distillation in order to recover the solvent and produce pure fatty and/or rosin acids. The fatty and/or rosin acids themselves can further be separated either by action of the solvent recovery column, if equipped to produce three or more product streams, or by an additional distillation step.

Some lignocellulosic materials will not yield appreciable resin acids. Those that do will yield varying amounts. According to the current invention, fatty and rosin acids, when they occur together may be converted to esters in their mixed state or separated by batch or continuous distillation prior to separately undergoing esterification. According to the current invention, separation by distillation of fatty and rosin acids may be accomplished via a dedicated batch or continuous distillation unit or via the solvent recovery unit if solvent extraction is utilized to extract them from pulping liquors. The decision as to whether to separate the rosin and fatty acids when they do both occur depends on the properties desired of the final ester fuel. Rosin acid based ester fuels have different properties than fatty acid based ester fuels. For example, rosin esters produce more particulate matter when they burn. Rosin esters have lower cetane numbers than fatty acid esters. However, rosin acids can serve to lower the freeze, cloud, pour, and/or cold flow plugging point of pure fatty acid ester fuels. Rosin esters can also have higher energy densities both due to their higher density as well as to their higher carbon and hydrogen to oxygen ratios.

Conversion of Fatty Acids to Esters

In terms of the production of ester fuels from fats and oils, manufacturers and researchers tend to focus on seed and animal based sources of fatty acids for the production of ester based fuels. Because oils derived from seed and animal fats represent the largest source of fatty acids and because these sources tend to produce fatty acids that are glycerated, the vast majority of processes developed and/or commercialized focus on processing glycerides to esters. The method of esterification according to the present invention becomes more optimal as the feedstock contains less glycerides.

While the conversion of glycerides to esters can be catalyzed by both acids and bases, most if not all commercial processing of glycerides to esters is done with base catalysis. Only acid catalysis can be used to convert fatty and/or rosin acids to ester fuels because base catalysts merely react with acids to form soaps. Very few commercial producers of ester fuels utilize wet chemical, acid catalyzed processing. This is partly due to the typical dominance of glycerides over "free" fatty acids in readily available fat and oil feedstocks. Undesirable side reactions between the catalyst and the unsaturated bonds in the fats and oils contaminate final ester products with undesirable anions such as sulfate and chlorine. Downstream separation difficulties from the esterification reactor are caused by the combination of soaps, glycerin and excess alcohol. Recovering excess alcohol becomes difficult as soaps tend to foam or form "crud" when heated to distillation temperatures and subjected to vapor agitation. Soap produced during reaction, neutralization, or bottoms separation inevitably contaminates the final product. Soap contamination of fuel esters in turn leads to poor low temperature performance of the fuel. Crystals form at relatively high temperatures plugging fuel filters and forming crud in storage and transportation tankage.

When wet chemical, acid catalyzed esterification is applied to glyceride-free fatty acids using equipment designed for transesterification, equilibrium constraints arise due to the effect of the water of reaction. Lack of full conversion of fatty acids to esters due to equilibrium constraints leads to excessive soap production during neutralization of the reaction mixture.

By applying heterogeneous reactive distillation technology to the esterification of glyceride-free and nearly glyceride-free fatty and/or rosin acids, we have been able to completely avoid soap formation, overcome equilibrium constraints, and reduce the alcohol recovery task to simply separating water, alcohol, and co-produced ethers.

This technology typically employs solid, acid catalysts of either the ceramic or ion-exchange resin bead type. Ceramic catalysts with high acidity or ion-exchange resins impregnated with sulfuric or other acids are typically used. Acid impregnated Ion-exchange resins display higher reactivity but suffer from a deactivation mechanism involving glycerides. Whereas fatty and rosin acids are able to adsorb, react with methanol, and desorb, a significant portion of any glycerides in the feed will absorb permanently and foul the catalyst. This has economic implications beyond catalyst life because just as the cost of glycerides increases as the free fatty acid content increases, the cost of fatty acids declines as the glyceride content increases. Most reactive distillation technologies immobilize the catalyst particles in ways that make change out prohibitively expensive in terms of labor, equipment, materials, catalyst support equipment, and downtime to perform on anything resembling a regular basis.

Applying the gas sparged, slurry reactor variant of reactive distillation disclosed in U.S. Pat. No. 5,536,856 (Harrison et al.) improves upon other approaches to reactive distillation by enabling the online addition or removal of catalyst via simple operations. The ability to change out catalyst while in operation allows for optimization of reactor performance against catalyst cost. It also allows for optimization of the glyceride/fatty acid cost function against the catalyst life and reactor performance functions.

According to the current invention, real-time steady state and dynamic optimization software is used to modulate manipulated variables in order to minimize competing cost and time functions. The steady state optimizer considers competing, control variable objectives such as catalyst cost, catalyst life, feed glyceride content, feed fatty and rosin acid distributions, temperatures, pressures, flows, alcohol loading, and alcohol water content in developing a set of near optimum desired setpoints for manipulated variables for which a cost function is minimized. The dynamic optimizer works to minimize the amount of time any of the control variables are away from their desired setpoint targets by continuously modulating the manipulated variables in a decoupled, multivariable sense.

Refining of Esters

Refining of recovered esters into various ester-based fuels is the final step in the process according to the invention. Suitable final products include ester-based fuel such as biodiesel and jet fuel. In addition, the biodiesel product may conform to industrial standards such as ASTM D-6751, or EN or IRS standards. The ester-based fuel can be optionally further processed by addition to petroleum-based fuels such as petroleum diesel or kerosene to form blends, such as B20, or may be sold as a non-blend, such as B100. In addition, processing according to the invention can yield an ester-based fuel with low glycerin, soap, alcohol, water, or sulfur content. By low is meant less than 5% by weight, and optionally less than 1%, and optionally less than 0.1% of any of the listed impurities, or combinations of the listed impurities. Ester-based fuels according to the invention can be processed to meet specifications for diesel, low sulfur diesel (LSD), ultra low sulfur diesel (ULSD), and biodiesel (BD).

EXAMPLES

The following examples are for illustrative purposes only and are not meant to be limiting. Various embodiments of the invention wherein all components listed above may or may not be used are possible under the current invention.

A sequential block diagram of an embodiment of the invention where fatty and/or rosin acids are separated from pulping liquors via gravity separation is presented in FIG. 1. The steps which alone or in combination comprise embodiments of the current invention are shown with continuous line outlines and grey fills. Dashed line outlines with white fills indicate steps which can be accomplished via numerous methods that themselves are not specific embodiments of the invention but which, by specific embodiments of the invention will be improved upon due to production of liquid ester fuels in addition to ethanol.

Referring to FIG. 1, lignocellulosic material 1 sourced from agricultural crop and/or forestry operations is first subjected to some form of comminution 2 in order to create a free flowing, solid feed to the hydrolysis/saccharification section 5. The hydrolysis/saccharification operation is composed of one or a combination of stages of operations selected from those known to those skilled in the art. Examples of suitable classes of stages include:

1. Alkaline Solution Pulping (Kraft)
2. Dilute Acid Pulping
3. Concentrated Acid Pulping
4. Organic Solvent Pulping
5. Hydrothermal Pulping
6. Ammonia, or Carbon Dioxide Pulping
7. Wet Oxidation Pulping
8. Enzymatic Hydrolysis
9. Bacterial Digestion Depending on the stage or stages of hydrolysis/saccharification chosen, various chemicals, water, solvents, steam, and/or enzymes 3 will also be fed to the hydrolysis/saccharification section 5. The purpose of the hydrolysis/saccharification section 5 is to free cellulose from lignin and to transform cellulose into soluble sugars such as glucose. The resulting sugar solution 6 is then mixed with yeast and/or other fermenting organisms 7 before undergoing batch or continuous fermentation 8. Fermentation yields the desired alcohol mixed with water. Water is separated from alcohol by use of distillation and/or molecular sieve adsorption to yield fuel ethanol 10. Water, $CO_2$, and solids 9 will also be produced. Water and solids, which include live and expired yeast, can be recycled, sewered, or otherwise dumped. It should be understood that the specific steps 1-10 can vary depending on the design of the fuel ethanol operation. It is not an object of the invention to apply the embodiments of the invention to any specific series of fuel ethanol production steps. Rather, steps 1-10 are intended to demonstrate how the embodiments of the invention relate to generalized fuel ethanol production from lignocellulosic feedstocks. In some cases, the various embodiments of the invention, as shown in grey fill, depend on the specific class of fuel ethanol technologies. Such instances are discussed below. Ethanol produced from the residual material can be used to make up a substantial amount of the C1-C8 alcohol of esterification according to the invention. By substantial amount is meant greater than 25% by weight, optionally greater than 50% by weight, and optionally greater than 90% by weight in various embodiments.

Depending on the stage or stages of hydrolysis/saccharification chosen for the hydrolysis/saccharification section 5, one or more streams of "pulping liquor" 11 containing liberated fatty and/or rosin acids will be created. This stream or streams may contain varying amounts of fatty and/or rosin acids in either acid or soap form. It may have acidic, neutral, or alkaline pH. It may be aqueous, aqueous containing a solvent, or all organic. Streams from different stages may be combined into one stream or treated separately. The desired fatty and/or rosin acids and/or their soaps may be in high enough concentration or may require further concentration via an evaporative concentration step 13. The water 14 from this step can be recycled back to the hydrolysis/saccharification step 5.

If the suitably concentrated pulping liquor is alkaline, it should be acidified 15 using a suitable inorganic or organic acid in order to "break" fatty and/or rosin soaps and enhance the lyophobicity of the fatty and/or rosin acids. The goal of the acidulation step is to obtain all fatty and/or rosin acids in their acid form.

Once the liquor is of suitable concentration and the fatty and/or rosin acids are predominantly in their acid form, gravity separation 16 is used to split the liquor into heavy 17 and light 18 streams. According to the current invention, gravity settling can be performed simply under the influence of the earth's gravitation or under the influence of centrifugation. Specially baffled separation vessels such as API or lamella settlers may be employed as well. U.S. Pat. No. 4,664,802 (Lee) discloses a liquid-liquid lamella separator suitable for use in the current invention. Gravity separation may be accomplished in a suitably sized vessel equipped with weirs and/or other devices that assist in separating the two phases. It may also be accomplished using centrifugation according to a variety of designs including that disclosed in U.S. Pat. No. 4,664,802 (Lee) incorporated herein by reference. It may also be accomplished using a lamella type separator such as those disclosed in U.S. Pat. Nos. 4,664,802 (Lee) and 4,151,084 (Probstein et al.). Other types of gravity separation enhancing equipment known to those skilled in the art can also be applied.

In some cases, three phases may also result with the middle layer being a "rag layer" consisting of material from the upper and lower phases in a stubborn emulsion. If the amount of desired fatty and/or rosin material in the rag layer is significant, it can be isolated separately and recycled back to the concentration or acidulation stage. This can either involve performing the gravity separation in batch fashion and directing the rag layer to separate storage during cutting of the vessel. It can also involve an additional continuous gravity separation stage in order to separate the rag layer from the upper or lower layer depending on which layer it exits the first stage with.

The heavy phase 17 from the gravity separation step 16 is redirected back to the fuel lignocellulose-to-fuel-ethanol process where it is utilized or disposed of according to the normal method associated with that process.

The fatty and/or rosin acid rich light phase 18 recovered from the gravity separation step may be of suitable composition for esterification or it may require removal of impurities or separation between the fatty and rosin acids. If additional impurity removal and/or fatty acid/rosin acid separation is desired, it is directed to a distillation step 19. This step can be designed to produce any number of products such as pure fatty acid and pure rosin acid streams according to batch and continuous distillation methods known to those skilled in the art. In general, rosin acids are higher boiling than fatty acids which are higher boiling that other impurities recovered at this point.

Once the fatty acids 20 and rosin acids 21 separated, if desired, and acceptably free of impurities, they can be fed to the esterification and purification section 23. A single C1-C8 alcohol or mixture thereof 22 is also fed to the esterification section. The method of esterification and purification along with several variations thereof are fully described in U.S. Pat. No. 5,536,856 (Harrison et al.) which is herein incorporated by reference. Esterification of the fatty and/or rosin acids via the method(s) of U.S. Pat. No. 5,536,856 leads to the production of fuel esters and water. Depending on the degree of saturation of the fatty acids and the content of rosin acids, these esters find use as fuels under various specifications including Biodiesel and jet fuel.

Figure 2:
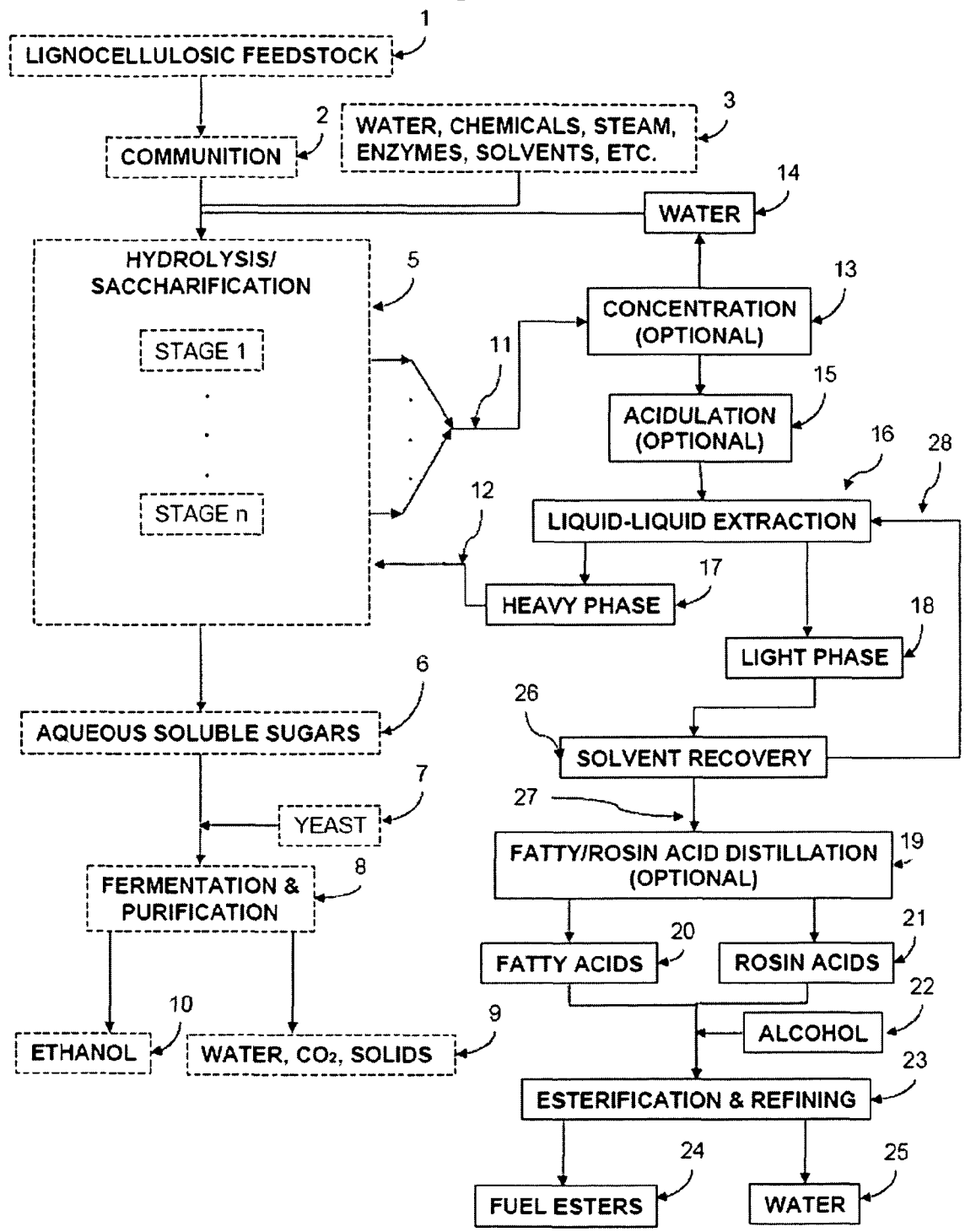
FIG. 2 is an overall sequential block diagram of the invention utilizing liquid-liquid extraction.

A sequential block diagram of an embodiment of the invention where fatty and/or rosin acids are separated from pulping liquors via liquid-liquid extraction is presented in FIG. 2. The steps and labels corresponding to those in FIG. 1 have the same meaning as those in FIG. 1. The lignocellulose-to-fuel-ethanol process is identical as that in FIG. 1. Fatty and/or rosin acid recovery and esterification is the same as in FIG. 1 up to step 16. In FIG. 2, the gravity separation step 16 of FIG. 1 is replaced with liquid-liquid extraction 16. The liquid-liquid extraction step 16 of FIG. 2 can be operated in batch or continuous mode. In batch mode, step 16 entails blending a predetermined amount of fresh and recovered solvent with the sufficiently concentrated and acidic "pulping liquor" and agitating. After a predetermined amount of time, agitation is ceased and the liquids are allowed to gravity settle into two or more phases. Gravity settling can be assisted according to methods described above or performed in the same vessel in which agitation took place. As with the process described by FIG. 1, the heavy phase 17 is directed back to the lignocellulose-to-fuel-ethanol process. The light phase 18 will be composed of the fatty and/or resin rich solvent.

In the continuous mode of step 16, a predetermined amount of solvent is fed to a point near the bottom of a trayed or packed column relative to the amount of concentrated and acidic pulping liquor that is fed to a point near the top. The liquid-liquid extraction is operated according to methods well known to those skilled in the art in order to produce a heavy mostly solvent free phase 17, and a lighter, fatty and/or rosin acid rich solvent phase 18.

In order to recover solvent for reuse in the extraction step 16, light phase 18 is subjected to batch or continuous distillation in the solvent recovery step 26. Normally, the solvent will be the lower boiling component and will therefore be taken as the distillate in the case of continuous distillation or as the first overhead product in the case of batch distillation. The mostly solvent free fatty and rosin acids 27 forming the distillation bottoms, in the continuous case, or the product remaining in the kettle after sufficient solvent removal, is then further processed to fuel esters as described above in the discussion of FIG. 1.

Figure 3:
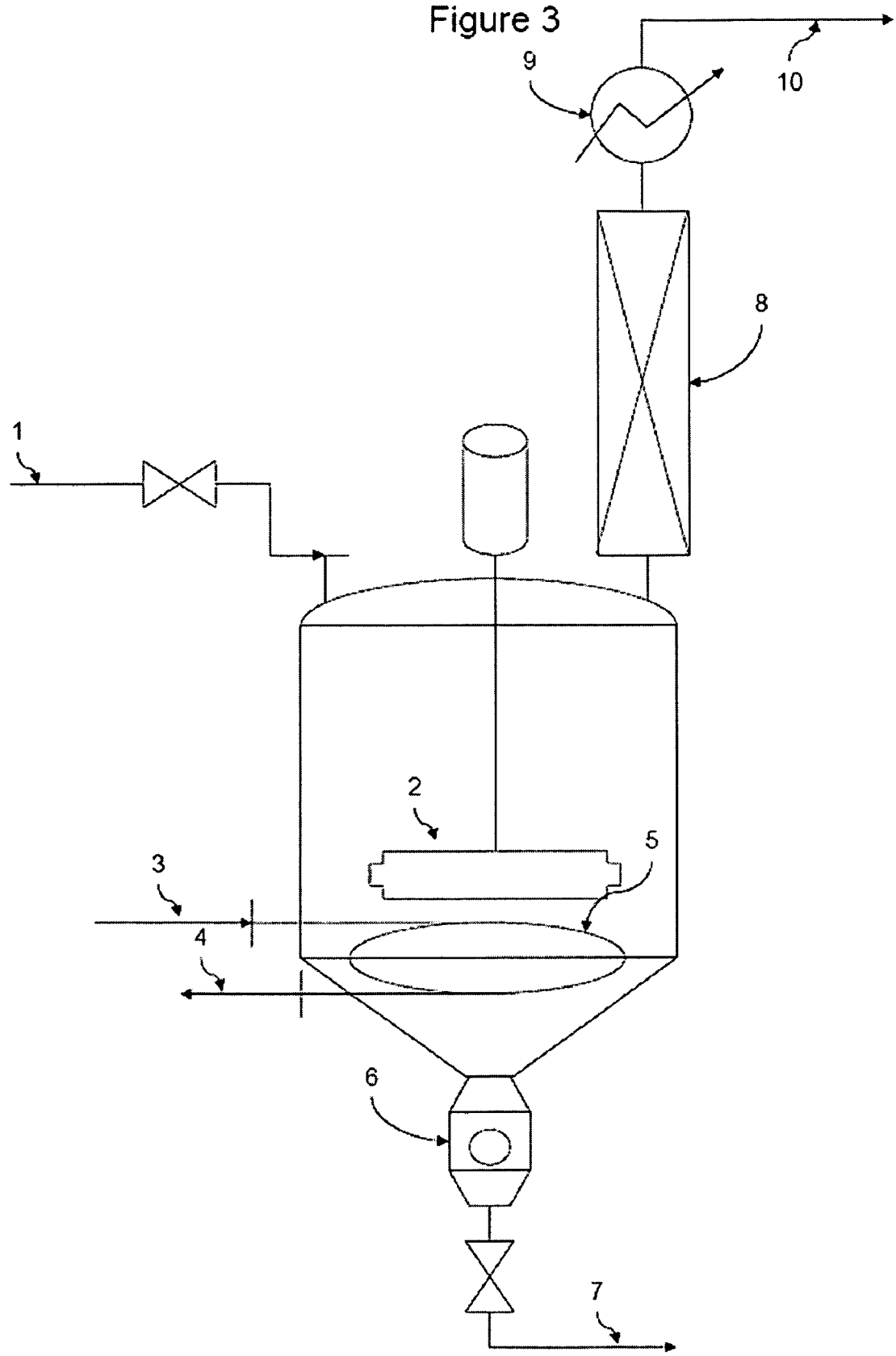
FIG. 3 is a schematic of batch extraction.

FIG. 3 shows a simplified schematic of a capital efficient embodiment of equipment suitable for performing batch extraction and solvent recovery according to the invention. According to FIG. 3, evaporative concentration 13, acidulation 15, solvent blending with liquor, agitation, separation, and solvent recovery distillation are all performed in the same vessel. Referring to FIG. 3, the vessel is equipped with a feed line 1 for charging it with pulping liquor, solvent, and acid. It is also equipped with a motor driven agitator 2. The vessel is equipped with a steam coil 5 and steam feed 3 and condensate return 4 lines. The sight glass 6 in combination with the vessel's cone bottom aid in performing successive sharp layer cuts as heavy, rag, and light phase layers are removed via bottom outlet 7. It is also equipped with a packed column 8 on its vapor line and a reflux partial condenser 9 for providing liquid reflux back down the column to aid in performing sharp distillation cuts as solvent is distilled off into vapor line 10. The sequence of operations is that described for FIG. 2. It should be understood that other embodiments of batch extraction and distillation are well known to those skilled in the art and in keeping with the spirit of the invention.

Figure 4:
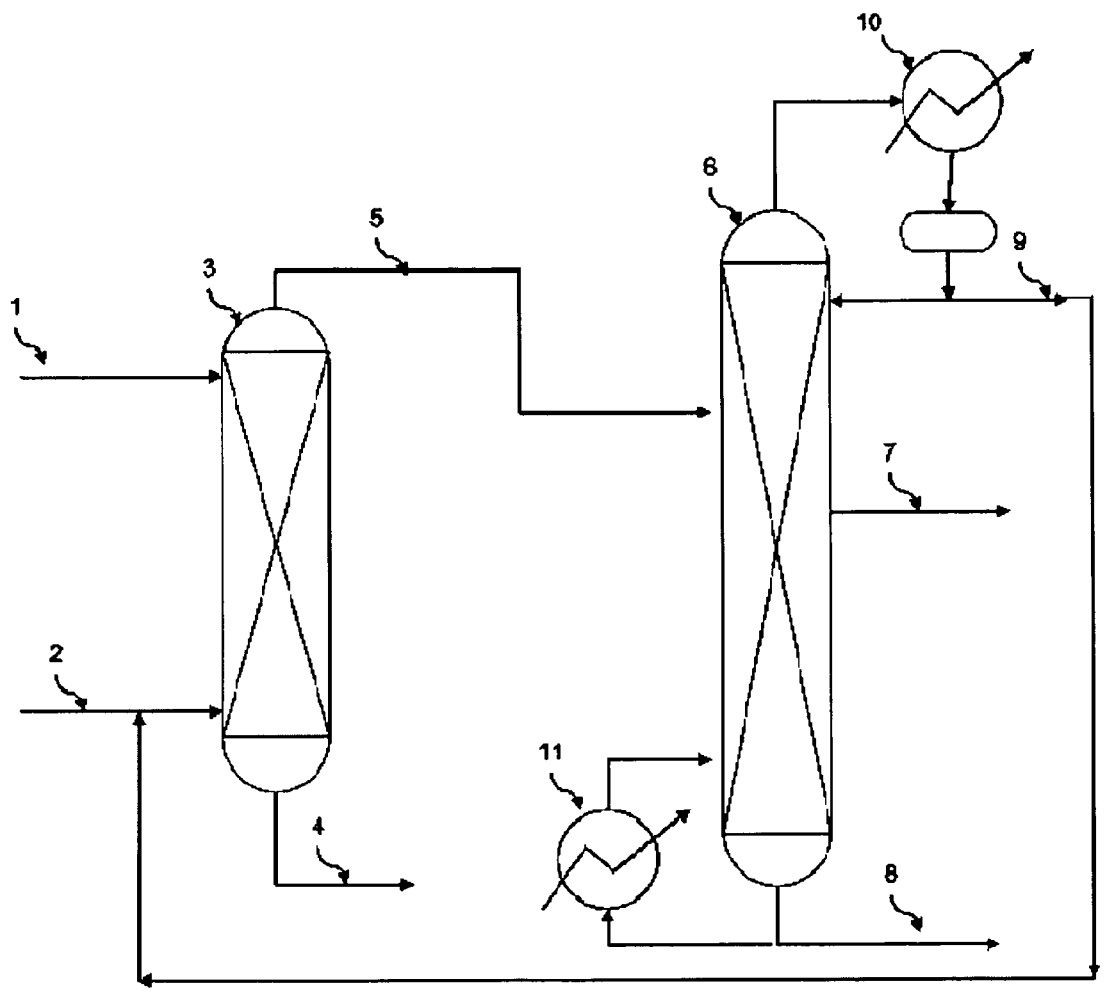
FIG. 4 is a schematic of continuous extraction.
Figure 5:
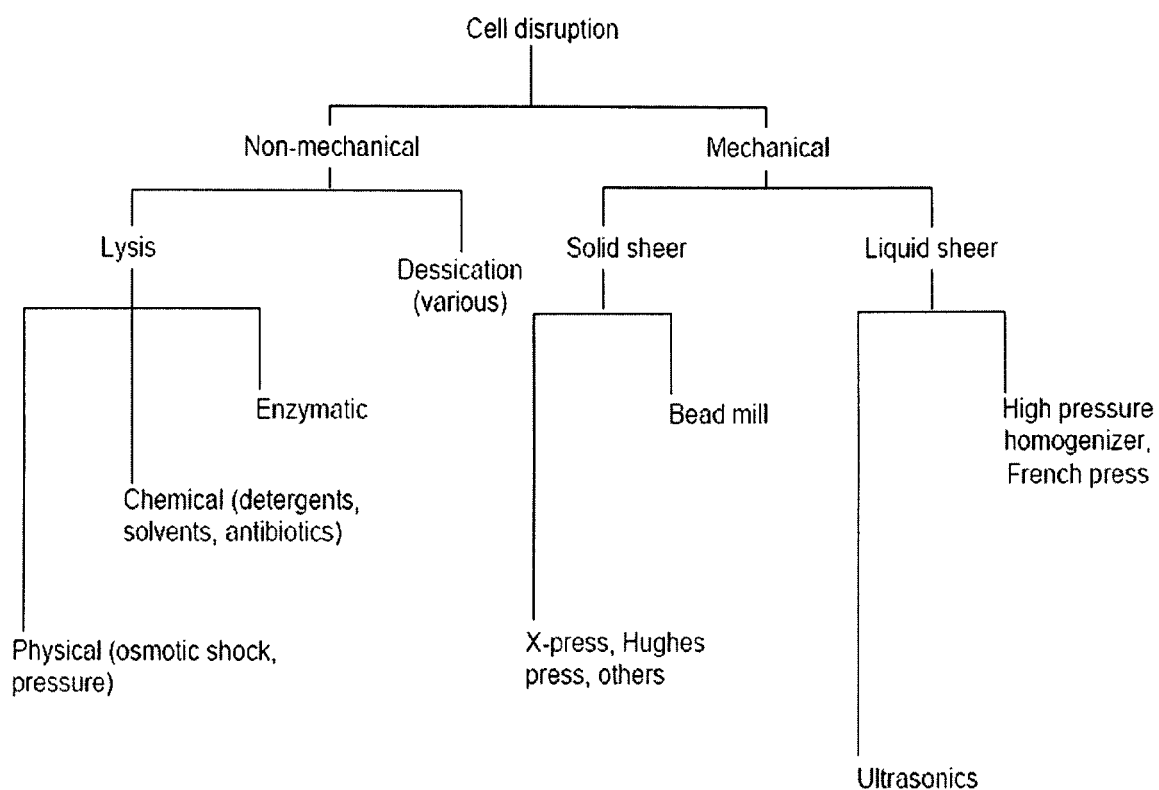
FIG. 5 categorizes various methods of cell disruption for comminution of starting material.
Figure 12:
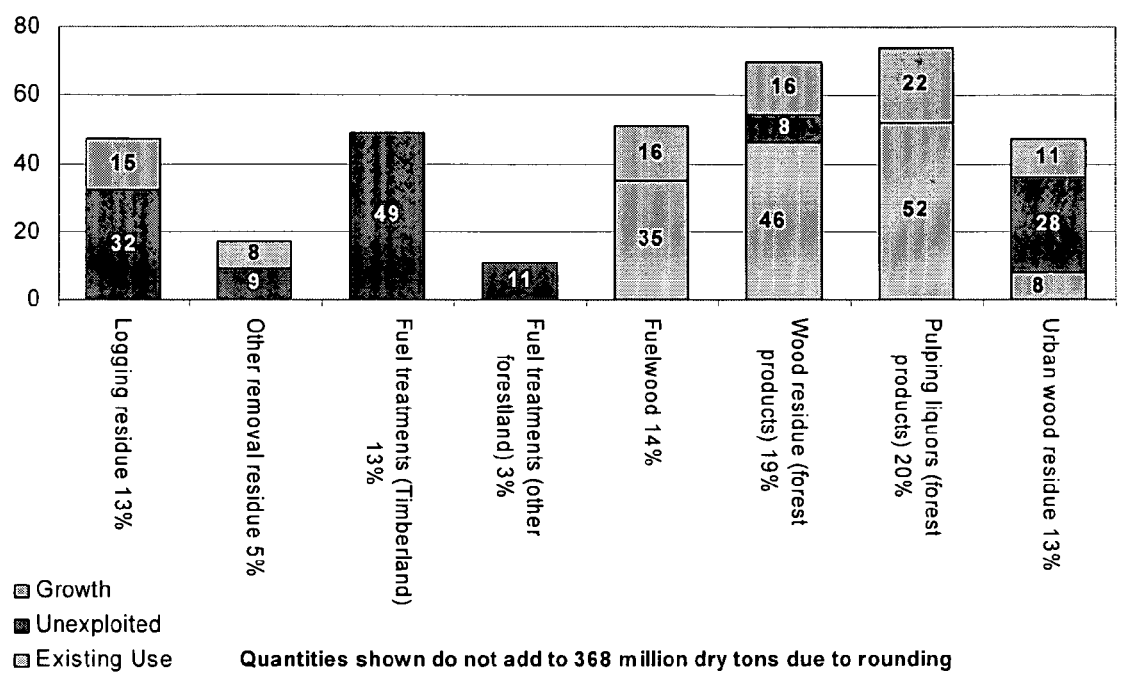
FIG. 12 is Table 6, which is the current availability of cellulose from forest resources.

FIG. 4 shows a simplified schematic of a capital efficient embodiment of equipment suitable for performing continuous extraction and solvent recovery according to the invention. In this embodiment, both solvent recovery and separation between fatty and rosin acids are accomplished in the same column. Sufficiently concentrated and acidic pulping liquor is fed to a location near the top of extraction column 3. Extraction column 3 contains packing or numerous trays in order to increase interfacial area between the two liquid phases and to affect stage wise, countercurrent separation. Recovered 9 and fresh solvent 2 are fed to a location near the bottom of extraction column 3. Due to the difference in density between the solvent and liquor phases, the solvent phase rises to the top of the column exiting via stream 5 while the liquor phase falls to the bottom of the column and exits via stream 4. On its way up the column, the solvent phase extracts fatty and/or rosin acids from the pulping liquor such that stream 5 contains most of the fatty and/or rosin acids fed to the column along with the liquor in stream 1.

Fatty and/or rosin acid rich solvent stream 5 is next fed to distillation column 6. Distillation column 6 can contain trays or packing in order to affect vapor-liquid equilibrium stage separation between upcoming vapor created by reboiler 11 and downcoming liquid created by reflux condenser 10. Due to the action of the vapor liquid equilibrium stages, pure solvent is recovered as distillate in stream 9 and recycled back to the extraction column, rosin- and solvent-free fatty acids are recovered in stream 7, and pure rosin acids are recovered in stream 8.

Various modifications to the distillation column in FIG. 4 are possible. For example, the feed to the column 5 could be heat exchanged with the bottoms from the column to improve energy efficiency. Additionally, side strippers and/or pump around coolers could be used to improve the sharpness of the splits between solvent, fatty acids, and rosin acids. It should be understood that other embodiments of continuous extraction solvent recovery, and fatty acid/rosin acid distillation are well known to those skilled in the art and in keeping with the spirit of the invention.

A sequential block diagram of an embodiment of the invention where fatty acids are recovered from concentrated algal pastes is given in FIG. 6. Algal paste 1 is obtained by any appropriate method in a concentration of about 15% solids or more. Alkali such as NaOH is added in order to produce a high pH mixture. The High pH mixture is subjected to heating and agitation 2. After some time, the high pH solution is diluted with water and allowed to settle into aqueous and oil layers containing saponified fatty acids 3. The oil layer is skimmed and then acidulated 4 with an acid such as $H_2SO_4$. That and subsequent heating and agitation are used to "break" the soaps 5 and yield fatty acids and salt water. The fatty acids from the soaps are recovered as an oil layer on top of a saltwater layer via settling and skimming 6. The cation free fatty acids are then esterified according to the method of the invention 7.

The above examples are for illustrative purposes only and are not meant to be limiting. Various embodiments of the invention wherein all components listed above may or may not be used are possible under the current invention. All references are incorporated by reference in their entirety.

The invention claimed is:

1. A process for the production of biodiesel ester based fuel from a concentration of algae comprising about 15% by weight solids, the process comprising:
   i) comminution of the concentration by solid or liquid shearing;
   ii) production of an organic layer comprising 30-40% fatty acid soaps via alkali lysing of the concentration;
   iii) collection of the organic layer via settling and skimming;
   iv) acidulation of the organic layer to produce free fatty acids;
   v) collection of the free fatty acids via settling and skimming;
   vi) addition of a C1-C8 alcohol to the fatty acid and heterogeneous esterification; and
   vii) refining of the resulting ester to produce an ester-based fuel.

2. The process according to claim 1, wherein following production of the organic layer residual material is further processed in fermentation and purification steps to yield ethanol.

3. The process according to claim 2, wherein the ethanol produced from the residual material makes up a substantial amount of the C1-C8 alcohol of step vi.

4. The process according to claim 1, wherein the organic layer is processed to contain between about 0.1% and about 30% by weight triglyceride and glycerin and greater than about 70% free fatty acid.

5. The process according to claim 1, wherein the C1-C8 alcohol of step vi is selected from methanol, ethanol, propanol, butanol, and mixtures thereof.

6. The process according to claim 1, wherein the esterification of step vi occurs via a gas sparged, slurry form of heterogeneous reactive distillation in a reaction chamber.

7. The process according to claim 6, wherein the gas sparged, slurry form of heterogeneous reactive distillation includes free particulate acidic ion exchange resin catalysts to catalyze esterification.

8. The process according to claim 7, wherein the reaction chamber of step vi comprises a vertical column reactor provided with a plurality of esterification trays mounted one above another, wherein the esterification trays are adapted to allow liquid phase to pass down the column reactor and vapor phase to pass up the column reactor.

9. The process according to claim 1, wherein the alcohol esterification of step vi occurs via a continuous reactive process.

10. The process according to claim 9, wherein the reaction chamber for step vi comprises a vertical column reactor provided with structured packing wherein the packing is adapted to support catalyst at one or more points in the reactor and to allow liquid phase to pass down and vapor phase to pass up the column reactor.

11. The process according to claim 1, wherein the yield of ester is greater than about 1.5% or greater than about 2% by weight of the concentration of algae.

12. The process according to claim 1, wherein the refining step v yields an ester-based fuel with low glycerin, soap, alcohol, and water content.

13. The process according to claim 12, wherein the glycerin, soap, alcohol, and water content are less than 0.5% by weight.

* * * * *

UNITED STATES PATENT AND TRADEMARK OFFICE
CERTIFICATE OF CORRECTION

| | | |
|---|---|---|
| PATENT NO. | : 8,105,398 B2 | Page 1 of 1 |
| APPLICATION NO. | : 12/172649 | |
| DATED | : January 31, 2012 | |
| INVENTOR(S) | : William Douglas Morgan | |

It is certified that error appears in the above-identified patent and that said Letters Patent is hereby corrected as shown below:

Column 20, in Claim 1, line 30:

Delete "ester based fuel"

Signed and Sealed this
Thirteenth Day of March, 2012

David J. Kappos
*Director of the United States Patent and Trademark Office*